(12) United States Patent
Holm et al.

(10) Patent No.: US 11,077,096 B2
(45) Date of Patent: *Aug. 3, 2021

(54) MODIFIED RELEASE COMPOSITIONS COMPRISING TACROLIMUS

(71) Applicant: Veloxis Pharmaceuticals A/S, Cary, NC (US)

(72) Inventors: Per Holm, Vanlose (DK); Tomas Norling, Lyngby (DK)

(73) Assignee: VELOXIS PHARMACEUTICALS INC., Cary, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/677,938

(22) Filed: Aug. 15, 2017

(65) Prior Publication Data

US 2018/0228779 A1    Aug. 16, 2018

Related U.S. Application Data

(63) Continuation of application No. 14/855,624, filed on Sep. 16, 2015, now Pat. No. 9,757,362, which is a continuation of application No. 14/079,443, filed on Nov. 13, 2013, now Pat. No. 9,161,907, which is a continuation of application No. 13/167,095, filed on Jun. 23, 2011, now Pat. No. 8,617,599, which is a continuation of application No. 10/569,862, filed as application No. PCT/DK2004/000573 on Aug. 30, 2004, now Pat. No. 8,591,946.

(60) Provisional application No. 60/529,793, filed on Dec. 15, 2003.

(30) Foreign Application Priority Data

| Aug. 29, 2003 | (DK) | PA 2003-01232 |
| Dec. 11, 2003 | (DK) | PA 2003-01837 |
| Jan. 21, 2004 | (DK) | PA 2004-00079 |
| Mar. 23, 2004 | (DK) | PA 2004-00463 |
| Mar. 23, 2004 | (DK) | PA 2004-00467 |

(51) Int. Cl.

| A61K 9/16 | (2006.01) |
| A61K 31/436 | (2006.01) |
| A61K 9/20 | (2006.01) |
| A61K 9/28 | (2006.01) |
| A61K 31/00 | (2006.01) |
| A61K 31/4745 | (2006.01) |
| A61K 9/10 | (2006.01) |
| A61K 31/439 | (2006.01) |
| A61K 9/00 | (2006.01) |

(52) U.S. Cl.
CPC .......... *A61K 31/436* (2013.01); *A61K 9/0053* (2013.01); *A61K 9/10* (2013.01); *A61K 9/1617* (2013.01); *A61K 9/1623* (2013.01); *A61K 9/1641* (2013.01); *A61K 9/1652* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2077* (2013.01); *A61K 9/2846* (2013.01); *A61K 31/00* (2013.01); *A61K 31/439* (2013.01); *A61K 31/4745* (2013.01); *A61K 9/1611* (2013.01); *A61K 9/2009* (2013.01); *A61K 9/2095* (2013.01); *A61K 9/2893* (2013.01); *Y10S 514/885* (2013.01)

(58) Field of Classification Search
CPC .......... A61K 9/14; A61K 9/141; A61K 9/143; A61K 9/145; A61K 9/146; A61K 9/16; A61K 9/1605; A61K 9/1682
See application file for complete search history.

(56) References Cited

U.S. PATENT DOCUMENTS

| 5,601,844 A | 2/1997 | Kagayama et al. |
| 6,168,806 B1 | 1/2001 | Lee et al. |
| 6,204,243 B1 | 3/2001 | Posanskl |
| 6,346,537 B1 | 2/2002 | Hata et al. |
| 6,387,918 B1 | 5/2002 | Yamanaka et al. |
| 6,440,458 B1 | 8/2002 | Yamashita et al. |
| 6,503,883 B1 | 1/2003 | Posanski |
| 6,576,259 B2 | 6/2003 | Yamashita et al. |

(Continued)

FOREIGN PATENT DOCUMENTS

| EP | 0184162 A2 | 6/1986 |
| EP | 0444659 A2 | 9/1991 |

(Continued)

OTHER PUBLICATIONS

Kjaergaard, et al., Priling—Multiple Core Encapsulation, http://www.niroinic.com/food_Chemical/prilling_encapsulation.asp.

(Continued)

*Primary Examiner* — Micah Paul Young

(74) *Attorney, Agent, or Firm* — Blank Rome LLP

(57) ABSTRACT

A modified release composition comprising tacrolimus releases less than 20% w/w of the active ingredient within 0.5 hours when subjected to an in vitro dissolution test using USP Paddle method and using 0.1 N HCl as dissolution medium and has increased bioavailability by effectively reducing or even avoiding the effects of CYP3A4 metabolism. The modified composition may be coated with an enteric coating; and/or may comprise a solid dispersion or a solid solution of tacrolimus in a hydrophilic or water-miscible vehicle and one or more modifying release agents; and/or may comprise a solid dispersion or a solid solution of tacrolimus in an amphiphilic or hydrophobic vehicle and optionally one or more modifying release agents.

13 Claims, No Drawings

(56) References Cited

U.S. PATENT DOCUMENTS

| | | | |
|---|---|---|---|
| 6,761,895 B2 | 7/2004 | Sawada et al. | |
| 6,884,433 B2 | 4/2005 | Yamashita et al. | |
| 6,884,436 B2 | 4/2005 | Kipp et al. | |
| 8,586,084 B2 | 11/2013 | Holm et al. | |
| 8,591,946 B2 * | 11/2013 | Holm | A61K 9/1652 424/469 |
| 8,617,599 B2 | 12/2013 | Holm et al. | |
| 8,623,410 B2 | 1/2014 | Holm et al. | |
| 8,623,411 B2 | 1/2014 | Holm et al. | |
| 8,664,239 B2 | 3/2014 | Gordon et al. | |
| 8,685,998 B2 | 4/2014 | Gordon et al. | |
| 8,889,185 B2 | 11/2014 | Holm et al. | |
| 8,889,186 B2 | 11/2014 | Holm et al. | |
| 9,161,907 B2 | 10/2015 | Holm | |
| 2002/0028240 A1 | 3/2002 | Sawada et al. | |
| 2003/0064097 A1 * | 4/2003 | Patel | A61K 9/1617 424/465 |
| 2003/0129250 A1 | 7/2003 | Batycky et al. | |
| 2003/0180352 A1 | 9/2003 | Patel et al. | |
| 2004/0121003 A1 * | 6/2004 | Chickering, III | A61K 9/145 424/465 |
| 2005/0169993 A1 | 8/2005 | Yamashita et al. | |
| 2005/0249799 A1 | 11/2005 | Jacob et al. | |
| 2006/0045865 A1 | 3/2006 | Jacob et al. | |
| 2006/0159766 A1 | 7/2006 | Jenkins et al. | |
| 2006/0177500 A1 | 8/2006 | Shin et al. | |
| 2006/0210638 A1 | 9/2006 | Liversidge et al. | |
| 2006/0287352 A1 | 12/2006 | Holm et al. | |
| 2007/0122482 A1 | 5/2007 | Holm et al. | |
| 2010/0008984 A1 | 1/2010 | Holm et al. | |
| 2010/0105717 A1 | 4/2010 | Gordon et al. | |
| 2011/0250277 A1 | 10/2011 | Holm et al. | |
| 2011/0251231 A1 | 10/2011 | Holm et al. | |
| 2011/0251232 A1 | 10/2011 | Holm et al. | |
| 2011/0256190 A1 | 10/2011 | Holm et al. | |
| 2011/0263632 A1 | 10/2011 | Holm et al. | |
| 2011/0275659 A1 | 11/2011 | Gordon et al. | |
| 2012/0029009 A1 | 2/2012 | Gordon et al. | |

FOREIGN PATENT DOCUMENTS

| | | | |
|---|---|---|---|
| EP | 1064942 A1 | 1/2001 | |
| EP | 1275373 A1 | 1/2003 | |
| EP | 1275381 A1 | 1/2003 | |
| EP | 1275831 A1 | 1/2003 | |
| JP | 62277321 A | 12/1987 | |
| JP | 6227732 A | 8/1994 | |
| WO | WO-9323022 A1 | 11/1993 | |
| WO | WO-199323022 A1 | 11/1993 | |
| WO | WO-9824418 A1 | 6/1998 | |
| WO | WO-199824418 A1 | 6/1998 | |
| WO | WO-9949863 A1 | 10/1999 | |
| WO | WO-199949863 A1 | 10/1999 | |
| WO | WO-01/37808 | 5/2001 | |
| WO | WO-200137808 A1 | 5/2001 | |
| WO | WO-01074359 A1 | 10/2001 | |
| WO | WO-2001074357 A1 | 10/2001 | |
| WO | WO-2001074359 A1 | 10/2001 | |
| WO | WO-0195939 A1 * | 12/2001 | A61K 9/4866 |
| WO | WO-200195939 A1 | 12/2001 | |
| WO | WO-03004001 A1 | 1/2003 | |
| WO | WO-2005004848 A1 | 1/2005 | |
| WO | WO-2005020993 A1 | 3/2005 | |
| WO | WO-2005020994 A1 | 3/2005 | |
| WO | WO-0550007 A1 | 6/2005 | |
| WO | WO-1275373 A2 | 6/2012 | |

OTHER PUBLICATIONS

Yang, et al., The Effect of Spray Mode and Chamber Geometry of Fluid-bed Coating equipment and Other Parameters on an Aqueous-based Ethylcellulose Coating (Abstract Only).

Non-Final Office Action dated Jan. 13, 2011 issued in U.S. Appl. No. 10/569,863.

Office Action dated Jun. 7, 2010 in U.S. Appl. No. 10/569,862.

U.S. Appl. No. 13/167,160, filed Jun. 23, 2011.

U.S. Appl. No. 13/167,281, filed Jun. 23, 2011.

U.S. Appl. No. 13/167,334, filed Jun. 23, 2011.

U.S. Appl. No. 13/167,381, filed Jun. 23, 2011.

U.S. Appl. No. 13/167,420, filed Jun. 23, 2011.

Cross, et al., Tacrolimus Once-Daily Formulation in the Prophylaxis of Transplant Rejection in Renal or Liver Allograft Receipients, Drugs, 2007, vol. 67, No. 13, pp. 1931-1943.

Davis, et al., An Oral Preparation to Release Drugs in the Human Colon, Br. J. Clin. Pharmac., 1982, vol. 14, pp. 405-408.

U.S. Appl. No. 13/167,095, filed Jun. 23, 2011.

Honbo et al., 1987, The oral dosage form of Fk-506, Transplantation Proceedings, vol. 19, No. 5, supplement 6, pp. 17-22.

Nishi et al., 2004, The Expression of Intestinal CYP3A4 in the Piglet Model, Transplantation Proceedings, vol. 36, No. 2, pp. 361-363.

Nishi, et al., 2004, The Colon Displays an Absorptive Capacity of Tacrolimus, Transplantation Proceedings, vol. 36, No. 2, pp. 364-366.

Sano et al., 2002, Oral FK 506 blood levels are elevated in pig short bowl model: Further investigations with co-administration of an intestinal CYP3A4 inhibitor, Transplantation Proceedings vol. 34, No. 3, pp. 1050-1051.

Tacrolimus (Systemic) Drugs.com, Drug Information Online; http://www.drugs.com/mmx/tacrolimus.hmtl; pp. 1-43; Printed on Oct. 5, 2009.

U.S. Appl. No. 13/029,304, filed Mar. 25, 2011.

U.S. Appl. No. 13/178,280, filed Jul. 7, 2011.

Barraclough, et al., Once—Versus Twice-Daily Tacrolimus are the Formulations Truly Equivalent?, Drugs 2011; 71 (12): 1561-1577.

Budde, et al., A Phase III Randomized Trial of Conversion to Once-daily Extended Release MeltDose® Tacrolimus Tablets (LCP-Tacro™) from Twice-daily Tacrolimus Capsules (Prograf®): Efficacy and Safety Results from an Analysis of Sub-populations, TTS Poster, 2012.

Bunnapradist, et al., Conversion From Twice-Daily Tacrolimus to Once-Daily Extended Release Tacrolimus (LCPT): The Phase III Randomized MELT Trial, American Journal of Transplantation Wiley Periodicals Inc., Received Jul. 17, 2012, revised Oct. 12, 2012 and accepted for publication Oct. 13, 2012.

Langone, LCP-Tacro Improves TAC-Induced Tremors: Preliminary Analysis of Switching STudy of Kidney TRansplant PAtients with Tremor to LCP-TacrO (STRATO): An Exploratory Study, Abstract for LCP-Tacro 3003 Protocol.

Nigro, et al., Flexible Dosing of Once-Daily LCP-Tacro Tablets: Morning Vs. Evening Randomized Crossover Chronopharmacokinetic Study, Poster presented at the AST/ESOT Joint Meeting, Oct. 12-14, 2012, Nice, France.

Nigro, et al., Improved Bioavailability and Pharmacokinetics of Tacrolimus With Novel Once-Daily LCP-Tacro™ Meltdose Formulation Versus Once-Daily Advagraf® Capsules, Poster presented at the AST/ESOT Joint Meeting, Oct. 12-14, 2012, Nice, France.

Strato Preliminary Results, Board Slides.

Weinberg, et al., Veloxis Announces Preliminary Analysis of the STRATO Study Suggesting Reduction in Tremor in Kidney Transplant Patients Switched from Twice-Dally Tacrolimus to Once-Daily LCP-Tacro™, Company Announcement No. 24/2012.

Declaration of Jon Weinberg, M.D. Under 37 C.F.R. § 1.132.

Bunnapradist, et al., Conversion From Twice-Daily Tacrolimus to Once-Daily Extended Release Tacrolimus (LCPT): The Phase III Randomized MELT Trial, American Journal of Transplantation, doi: 10.1111/ajt.12035, 2012.

Declaration of John Weinberg, M.D. under 37 C.F.R. § 1.132.

Nigro, et al., Flexible dosing of once-daily LCP-Tacro tablets: morning vs. evening randomized crossover chronopharmacokinetic study, AST/ESOT Joint Meeting, Oct. 12-14, 2012, Nice, France.

Nigro, et al., Improved bioavailability and pharmacokinetics of tacrolimus with novel once-daily LCP-Tacro™ Meltdose formulation versus once-dally Advagraf® capsules, AST/ESOT Joint Meeting, Oct. 12-14, 2012, Nice, France.

(56) References Cited

OTHER PUBLICATIONS

Office Action dated Mar. 31, 2010 in U.S. Appl. No. 10/569,863.
Official Action for U.S. Appl. No. 10/569,863, dated Oct. 8, 2009; 13 pages.
Tacrolimus (Systemic) Drugs.com, Drug Information Online, http://www.drugs.com/mmx/tacrolimus.html; pp. 1-43, printed Oct. 5, 2009.
Yang et al., Int. J. Pharmaceutics, 1992, vol. 86(2-3), 247-257; Abstract only, p. 1 of 1.
Nishi, et al., 2004, TThe Colon Displays an Absorptive Capacity of Tacrolimus, Transplantation Proceedings, vol. 36, No. 2, pp. 364-366.
Sano, et al., 2002, Oral FK 506 Blood Levels, Transplantation Proceedings, vol. 34, No. 3, pp. 1050-1051.

\* cited by examiner

MODIFIED RELEASE COMPOSITIONS COMPRISING TACROLIMUS

This application is a continuation of U.S. patent application Ser. No. 14/855,624 filed Sep. 16, 2015, which is a continuation of U.S. patent application Ser. No. 14/079,443, filed Nov. 13, 2013, which is a continuation of U.S. patent application Ser. No. 13/167,095, filed Jun. 23, 2011, which is a continuation of U.S. patent application Ser. No. 10/569,862, filed Feb. 27, 2006, which is the U.S. national phase of International Application No. PCT/DK2004/000573, filed Aug. 30, 2004, which claims the benefit of U.S. Provisional Application No. 60/529,793 (filed Dec. 15, 2003) and Danish Patent Application Nos. PA 2003-01232 (filed Aug. 29, 2003), PA 2003-01837 (filed Dec. 11, 2003), PA 2004-00079 (filed Jan. 21, 2004), PA 2004-00463 (filed Mar. 23, 2004), and PA 2004-00467 (filed Mar. 23, 2004), each of which is incorporated herein by reference in its entirety.

The present invention relates to a pharmaceutical composition and/or dosage forms, preferably oral unit dosage forms, comprising tacrolimus or an analogue thereof having a modified release profiles when subjected to a conventional dissolution method, which is believed to reflect the actual rate and timing of release of active ingredient in vivo, the novel composition effectively reducing or even avoiding the effects of CYP3A4 metabolism.

BACKGROUND OF THE INVENTION

Tacrolimus, also known as FK-506 or FR-900506, has the chemical tricyclic structure shown below:

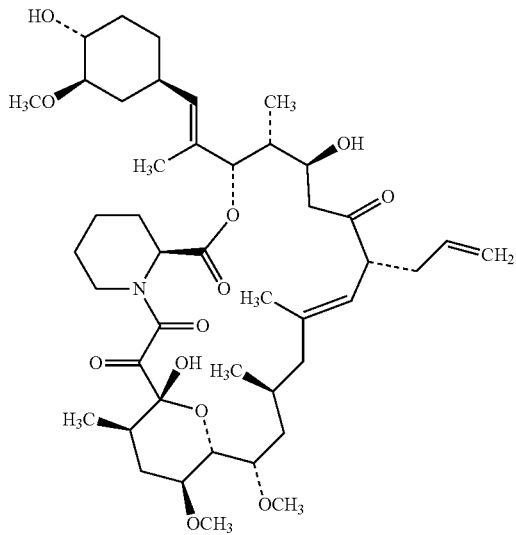

corresponding to $C_{44}H_{69}NO_{12}$. Tacrolimus appears in the form of white crystals or crystalline powder. It is practically insoluble in water, freely soluble in ethanol and very soluble in methanol and chloroform.

The preparation of tacrolimus is described in EP-A-0 184 162 and analogues of tacrolimus are disclosed e.g. in EP-A-0 444 659 and U.S. Pat. No. 6,387,918, which are both hereby incorporated by reference.

Tacrolimus is a macrolide compound with useful immunosuppressive activity, antimicrobial activity and other pharmacological activities and is of value for the treatment or prevention of rejection reactions by transplantation of organs or tissues, graft versus host diseases, autoimmune diseases and infectious diseases. Tacrolimus prolongs the survival of the host and transplanted graft in animal transplant models of liver, kidney, heart, bone marrow and small bowel and pancreas, lung and trachea, skin, cornea and limb.

In animals, tacrolimus has been demonstrated to suppress some humoral immunity and, to a greater extent, cell-mediated reactions such as allograft rejection, delayed type hypersensitivity, collagen-induced arthritis, experimental allergic encephalomyelitis and graft-versus-host disease.

Tacrolimus inhibits T-lymphocyte activation, although the exact mechanism of action is unknown. Experimental evidence suggest that tacrolimus binds to an intracellular protein, FKBP-12. A complex of tacrolimus-FKBP-12, calcium, calmodulin, and calcineurin is then formed and the phosphatase activity of calcineurin inhibited. This effect may prevent the dephosphorylation and translocation of nuclear factor of activated T-cells, a nuclear component thought to initiate gene transcription for the formation of lymphokines. The net result is the inhibition of T-lymphocyte activation, i.e. immunosuppression.

Tacrolimus is extensively metabolized by the CYP3A4 isoenzyme in the gut wall and liver. Therefore, drugs that affect this isoenzyme may influence absorption and the subsequent elimination of systemically absorbed tacrolimus. Inhibitors of CYP3A4 may increase tacrolimus levels, while inducers of CYP3A4 may increase the metabolism of tacrolimus and decrease tacrolimus levels. Accordingly, tacrolimus may be administered together with one or more CYP3A4 inhibitors in order to improve the overall bioavailability.

Usually tacrolimus is administered orally and is therefore absorbed from the gastrointestinal tract. It has been observed that the absorption is negatively influenced by the simultaneous ingestion of food. Thus, the rate and extent of tacrolimus absorption were greatest under fasted conditions.

In general, it is known that the absorption and bioavailability of a therapeutically active substance can be affected by a variety of factors when administered orally. Such factors include the presence of food in the gastrointestinal tract and, in general, the gastric residence time of a drug substance is significantly longer in the presence of food than in the fasted state. If the bioavailability of a drug substance is affected beyond a certain point due to the presence of food in the gastrointestinal tract, the drug substance is said to exhibit a food effect. Food effects are important because absorption and hence the plasma levels becomes highly variable depending on food intake. Absorption into the bloodstream may be adversely affected to the point that the patient risks insufficient absorption to remedy the condition for which the drug was administered. On the other hand, the very high peak concentrations seen at fasted conditions occasionally, may very well induce significant side effects, of nephro- or neuro-toxic origin, as well as GI side-effects and others.

Absorption of tacrolimus from the gastrointestinal tract after oral administration is rapid with a mean time-to-peak concentration ($t_{max}$) of approximately 1-2 hours after administration to healthy subjects or kidney or liver transplanted patients, but incomplete and variable. The bioavailability is generally as low as at the most about 20% after oral administration.

Frequently observed side effects are vomiting and nausea but side effects like tremor, headache, hypertension, renal dysfunction, hyperkalemia, hypomagnesaemia, hyperglycemia, insomnia, diarrhea, constipation, abdominal pain, nephrotoxicity and neurotoxicity are also observed.

For oral administration, tacrolimus is currently formulated and marketed as soft gelatine capsules comprising the equivalent of 0.5, 1 or 5 mg anhydrous tacrolimus and marketed under the trade name Prograf® and Protropic®. The recommended initial oral dose is from about 0.1 to 0.2 mg/kg/day in patients. The dose aims at a certain trough plasma level from about 5 to about 20 ng/ml. Prograf® is indicated for the prophylaxis of organ rejection in patients receiving allogeneic liver or kidney transplants.

There remains a need for novel pharmaceutical compositions and/or dosage forms comprising tacrolimus exhibiting enhanced bioavailability. An increased bioavailability may allow a reduction in the dosage units taken by a patient, e.g. down to a single dose daily, and may also reduce or negate the need for food to be takes simultaneously with the dosage form thereby allowing patients more freedom on when the drug is taken. Furthermore, it is contemplated that fluctuations in the plasma concentration versus time profile may be significantly reduced. Further, enhanced bioavailability may also result in a more reproducible (i.e. less variable compared to that of Prograf®) release profile.

BRIEF SUMMARY OF THE INVENTION

The inventors have found that the bioavailability of tacrolimus is significantly increased when tacrolimus is administered to a mammal in a modified or controlled release composition providing a rate and a timing of release of active ingredient, i.e. an in vivo release profile, effectively reducing or even avoiding the effects of CYP3A4 metabolism.

It is believed that conventional in vitro dissolution methods correlate to or at least reflect the actual in vivo modified release profile in man. In accordance herewith, the present invention provides, in its first aspect, a solid pharmaceutical composition comprising an active ingredient selected among tacrolimus and analogues thereof, wherein less than 20% w/w of the active ingredient is released within 0.5 hours, when subjected to an in vitro dissolution test using USP Paddle method and using 0.1 N HCl as dissolution medium. This modified release profile is obtained by providing a pharmaceutical composition which i) is coated with an enteric coating; and/or
ii) comprises a solid dispersion or, preferably, a solid solution of active ingredient, i.e. tacrolimus or an analogue thereof, in a hydrophilic or water-miscible vehicle and one or more modifying release agents; and/or
iii) comprises a solid dispersion or, preferably, a solid solution of active ingredient, i.e. tacrolimus or an analogue thereof, in an amphiphilic or hydrophobic vehicle and optionally one or more modifying release agents.

In a further aspect, the invention relates to solid dosage forms, especially oral dosage forms, comprising the composition of the invention, the solid dosage forms exhibiting a modified release profile. Delaying the release of tacrolimus to the distal part of duodenum may reduce the drug related gastro-intestinal related side effects and the relatively high degree of metabolism in the proximal part of the gastrointestinal tract (CYP3A4 mediated metabolism). This can be done without loosing systemic bioavailability due to the unique compositions of the invention, preferably compositions comprising the active ingredient fully or partly dissolved in a vehicle to form a solid dispersion and/or a solid solution at ambient temperature.

In yet further aspects, the invention relates to use of the present pharmaceutical composition to enhance the oral bioavailability of tacrolimus, to use of the present composition in the preparation of medicines or medicaments, especially in the preparation of useful solid dosage forms.

DETAILED DESCRIPTION OF THE INVENTION

Definitions

As used herein, the term "active ingredient" or "active pharmaceutical ingredient" means any component that is intended to furnish pharmacological activity or other direct effect in the diagnosis, cure, mitigation, treatment, or prevention of disease, or to affect the structure or any function of the body of man or other animals. The term includes those components that may undergo chemical change in the manufacture of the drug product and are present in the drug product in a modified form intended to furnish the specified activity or effect.

In the present context, the term "hydrophilic" describes that something 'likes water', i.e. a hydrophilic molecule or portion of a molecule is one that typically is electrically polarized and capable of forming hydrogen bonds with water molecules, enabling it dissolve more readily in water than in oil or other "non-polar" solvents.

In the present context, the term "amphiphilic" describes a molecule (as a surfactant) having a polar water-soluble group attached to a water-insoluble hydrocarbon chain. Thus, one end of the molecule is hydrophilic (polar) and the other is hydrophobic (non-polar).

In the present context, the term "hydrophobic" denotes a compound tending to be electrically neutral and non-polar, and thus preferring other neutral and nonpolar solvents or molecular environments.

As used herein, the term "vehicle" means any solvent or carrier fluid in a pharmaceutical product that has no pharmacological role. For example, water is the vehicle for xilocaine and propylene glycol is the vehicle for many antibiotics.

In the present context, the term "solid dispersion" denotes a drug or active ingredient or substance dispersed on a particulate level in an inert vehicle, carrier, diluent or matrix in the solid state, i.e. usually a fine particulate dispersion.

In the present context, the term "solid solution" denotes a drug or active ingredient or substance dissolved on a molecular level in an inert vehicle, carrier, diluent or matrix in the solid state.

As used herein, the term "analogue" means a chemical compound that is structurally similar to another.

The term "drug" means a compound intended for use in diagnosis, cure, mitigation, treatment, or prevention of disease in man or other animals.

In this context, the term "dosage form" means the form in which the drug is delivered to the patient. This could be parenteral, topical, tablet, oral (liquid or dissolved powder), suppository, inhalation, transdermal, etc.

As used herein, the term "bioavailability" denotes the degree means to which a drug or other substance becomes available to the target tissue after administration.

As used herein, the term "bioequivalency" denotes a scientific basis on which generic and brand name drugs are compared with one another. For example, drugs are bioequivalent if they enter circulation at the same rate when given in similar doses under similar conditions. Parameters often used in bioequivalence studies are $t_{max}$, $C_{max}$, $AUC_{0\text{-}infinity}$, $AUC_{0\text{-}t}$. Other relevant parameters may be $W_{50}$, $W_{75}$ and/or MRT. Accordingly, at least one of these parameters may be applied when determining whether bioequivalence is present. Furthermore, in the present context, two compositions are regarded as bioequivalent if the value of the parameter used is within 80-125% of that of Prograf® or a similar commercially available tacrolimus-containing product used in the test.

In the present context "$t_{max}$" denotes the time to reach the maximal plasma concentration ($c_{max}$) after administration; $AUC_{0\text{-}infinity}$ denotes the area under the plasma concentration versus time curve from time 0 to infinity; $AUC_{0\text{-}t}$ denotes the area under the plasma concentration versus time curve from time 0 to time t; $W_{50}$ denotes the time where the plasma concentration is 50% or more of $C_{max}$; $W_{75}$ denotes the time where the plasma concentration is 75% or more of $C_{max}$; and MRT denotes mean residence time for tacrolimus (and/or an analogue thereof).

In this context, the term "medicine" means a compound used to treat disease, injury or pain. Medicine is justly distributed into "prophylactic," i.e. the art of preserving health, and "therapeutic", i.e. the art of restoring health.

In the present context, the terms "controlled release" and "modified release" are intended to be equivalent terms covering any type of release of tacrolimus from a composition of the invention that is appropriate to obtain a specific therapeutic or prophylactic response after administration to a subject. A person skilled in the art knows how controlled release/modified release differs from the release of plain tablets or capsules. The terms "release in a controlled manner" or "release in a modified manner" have the same meaning as stated above. The terms include slow release (that results in a lower $C_{max}$ and later $t_{max}$, but $t_{1/2}$ is unchanged), extended release (that results in a lower $C_{max}$, later $t_{max}$, but apparent $t_{1/2}$ is longer); delayed release (that result in an unchanged $C_{max}$, but lag time and, accordingly, $t_{max}$ is delayed, and $t_{1/2}$ is unchanged) as well as pulsatile release, burst release, sustained release, prolonged release, chrono-optimized release, fast release (to obtain an enhanced onset of action) etc. Included in the terms is also e.g. utilization of specific conditions within the body e.g. different enzymes or pH changes in order to control the release of the drug substance.

In this context, the term "erosion" or "eroding" means a gradual breakdown of the surface of a material or structure, for example of a tablet or the coating of a tablet.

The present invention provides pharmaceutical compositions and solid dosage forms for improved treatment of conditions that respond to tacrolimus treatment, especially compositions and dosage forms providing modified release of the active ingredient in order to enhance the bioavailability thereof.

The active ingredient in the inventive compositions is preferably tacrolimus or any analogue or derivative of tacrolimus, which exhibits either a pharmacological or a therapeutical activity, which is at least equivalent to that of tacrolimus (FK-506 or FR-900506). However, within the scope of the present invention is tacrolimus in any physical form (crystals, amorphous powder, any possible polymorphs, any possible solvates including the hydrate, anhydrate, complexes thereof etc.). Included is also any analogue, derivative or active metabolite of tacrolimus, pharmaceutically acceptable salts, solvates, complexes and prodrugs thereof.

Thus, in a preferred embodiment, the present invention provides a solid pharmaceutical composition comprising an active ingredient selected among tacrolimus and analogues thereof, wherein less than 20% w/w of the active ingredient is released within 0.5 hours, when subjected to an in vitro dissolution test using USP Paddle method and using 0.1 N HCl as dissolution medium; preferably wherein less than 20% w/w, more preferably less than 10% w/w of the active ingredient is released within 3 hours.

It is believed that such a release profile significantly enhances the bioavailability of tacrolimus in mammals, since all or a major part of the active ingredient is in fact released in the gastrointestinal tract in such as manner that CYP3A4 metabolism is substantially avoided or at least significantly reduced. Further, it is contemplated that this effect is correlated to or at least reflected to the in vitro dissolution profile of the solid pharmaceutical composition and/or dosage forms of the invention, which profile is easily found when subjecting the composition and/or dosage form to a conventional in vitro dissolution method according to e.g. USP. It is believed that any USP in vitro dissolution method is useful for the present purpose.

For example, the solid pharmaceutical composition of the invention releases at least 50% w/w of the active ingredient within 4 hours, preferably within 2.5 hours, when subjected to an in vitro dissolution test using USP Paddle method and using 0.1N HCl as dissolution medium during the first 2 hours and then using a dissolution medium having a pH of 6.8.

Using a less conventional dissolution medium, the composition of the invention releases less than 50 w/w %, especially less than 40 w/w %, of the active ingredient within 8 hours, preferably within 15 hours, when subjected to an in vitro dissolution test using USP Paddle method and an aqueous dissolution medium adjusted to pH 4.5 with 0.005% hydroxypropylcellulose.

The desired modified release profile of the pharmaceutical composition may be provided by
  i) coating the composition with an enteric coating; and/or
  ii) using a pharmaceutical composition comprising a solid dispersion or solid solution of active ingredient, i.e. tacrolimus or an analogue thereof, in a hydrophilic or water-miscible vehicle and one or more modifying release agents; and/or
  iii) using a pharmaceutical composition comprising a solid dispersion or solid solution of active ingredient, i.e. tacrolimus or an analogue thereof, in a hydrophobic vehicle and optionally one or more modifying release agents.

In one embodiment of the invention, there is provided a modified release tacrolimus-containing pharmaceutical composition which is entero-coated as described herein.

In another embodiment of the invention, there is provided a modified release tacrolimus-containing pharmaceutical composition having the active ingredient dissolved or dispersed in a hydrophobic vehicle as described herein, preferably in an oil, an oily material, a wax or a fatty acid derivative, more preferably a wax having a low melting point such as for example glyceryl monostearate.

In yet another embodiment of the invention, there is provided a modified release tacrolimus-containing pharmaceutical composition having the active ingredient dissolved or dispersed in a hydrophilic or water-miscible vehicle as described herein, preferably a vehicle selected among polyethylene glycols, polyoxyethylene oxides, poloxamers, polyoxyethylene stearates, poly-epsilon caprolactone, polyglycolized glycerides such as Gelucire®, and mixtures thereof, more preferably polyethylene glycol optionally in mixture with a poloxamer. A specific example of a useful mixture is a mixture of 70 w/w % polyethylene glycol 6000 (PEG6000) and 30 w/w % poloxamer 188.

In a further aspect, the present invention relates to a pharmaceutical composition in particulate form comprising tacrolimus and/or an analogue thereof together with one or more pharmaceutically acceptable excipients, wherein the composition upon oral administration to a mammal in need thereof exhibits an AUC/AUC$_{Prograf®}$ value of at least about 1.3, the AUC values being determined under similar conditions.

As it appears from the examples herein the bioavailability obtained after administration of a composition according to the invention is markedly improved. Thus, in specific embodiments, the AUC/AUC$_{Prograf®}$ value is at least about 1.5 such as about 1.75 or more, about 1.8 or more, about 1.9 or more, about 2.0 or more, about 2.5 or more, about 2.75 or more, about 3.0 or more, about 3.25 or more, about 3.5 or more, about 3.75 or more, about 4.0 or more, about 4.25 or more, about 4.5 or more, about 4.75 or more or about 5.0 or more, the AUC values being determined under similar conditions.

After oral administration of a pharmaceutical composition according to the present invention it is contemplated that the plasma concentration versus time profile show an extended period of time in which the plasma concentration is maintained within the therapeutic window (i.e. the plasma concentration leads to a therapeutic effect) without leading to serious unwanted side effects. Thus, a reduction in peak concentration is also observed. Accordingly, the invention relates to a pharmaceutical composition in particulate form comprising tacrolimus together with one or more pharmaceutically acceptable excipient, wherein the composition upon oral administration to a mammal in need thereof releases tacrolimus in a controlled manner and exhibits a $C_{max}$ that is at the most about 80% of that of $C_{max}$ for Prograf® tablets such as, e.g., at the most about 75%, at the most about 70%, at the most about 65%, at the most about 60%, at the most about 55%, at the most about 50%, at the most about 45% or at the most about 40%.

In the present context the terms controlled release and modified release are intended to be equivalent terms covering any type of release of tacrolimus from a composition of the invention that is appropriate to obtain a specific therapeutic or prophylactic response after administration to a subject. A person skilled in the art knows how controlled release/modified release differs from the release of plain tablets or capsules. The terms "release in a controlled manner" or "release in a modified manner" have the same meaning as stated above.

The terms controlled release/modified release include slow release (that results in a lower $C_{max}$ and later $t_{max}$, but $t_{1/2}$ is unchanged), extended release (that results in a lower $C_{max}$, later $t_{max}$, but apparent $t_{1/2}$ is longer); delayed release (that result in an unchanged $C_{max}$, but lag time and, accordingly, $t_{max}$ is delayed, and $t_{1/2}$ is unchanged) as well as pulsatile release, burst release, sustained release, prolonged release, chrono-optimized release, fast release (to obtain an enhanced onset of action) etc. Included in the terms is also e.g. utilization of specific conditions within the body e.g. different enzymes or pH changes in order to control the release of the drug substance.

To be more specific, after oral administration to a mammal, including a human, of a pharmaceutical composition according to the present invention containing a dose of 5 mg tacrolimus, tacrolimus is released in a controlled manner and will exhibit a $C_{max}$ that is at the most about 30 ng/ml such as, e.g. at the most about 25 ng/ml or at the most about 20 ng/ml.

However, a reduction in peak concentration may not lead to a decrease in therapeutic effect as long as the plasma concentration of tacrolimus is maintained within the therapeutic window. Accordingly, the present invention also relates to a pharmaceutical composition, wherein $W_{50}$ is at least about 2 hours, such as, e.g., at least about 3 hours, at least about 4 hours, at least about 5 hours, at least about 6 hours, at least about 7 hours, at least about 8 hours, at least about 9 hours, about 10 hours or more, about 11 hours or more, about 12 hours or more, about 13 hours or about 14 hours or more.

Furthermore or moreover, a composition according to the invention has a $C_{diff}=[C_{max}-C_t(t=12 \text{ hours})]$ that is less than that of Prograf® under the same conditions. If $C_{diff}$ for Prograf® is set to 100 then $C_{diff}$ of a composition according to the invention is normally 90 or less such as, e.g., about 85 or less, about 80 or less, about 75 or less, about 70 or less, about 65 or less, about 60 or less, about 55 or less, about 50 or less, about 45 or less or about 40 or less.

More specifically, after oral administration to a mammal, including a human, of a pharmaceutical composition of the invention containing of 5 mg of tacrolimus, tacrolimus is released in a controlled manner and exhibits a $C_{diff}$ of about 20 ng/ml or less such as, e.g., about 15 ng/ml or less, about 13 ng/ml or less or about 10 ng/ml or less.

A pharmaceutical composition according to the invention releases tacrolimus in a controlled manner in order to extend the therapeutic action of tacrolimus. In one aspect the release may be pH dependant, i.e. the release predominantly takes place after passage of the stomach. Such a pH dependent release is mainly provided by means of enteric coating material as described herein. The release may also be pH independent, e.g. by providing the composition with a controlled release coating such as, e.g. a cellulose based coating like e.g. ethylcellulose or by providing the composition in the form of a matrix composition such as, e.g., a hydrophilic cellulose polymer matrix type e.g. based on HPMC. A combination may of course also be employed.

In general, the change in bioavailability and/or the changes in other bioavailability related parameters are normally determined by in vivo studies in a suitable animal model testing the compositions in question together with e.g. Prograf® or a similar commercially available tacrolimus-containing product. The use of a dog model for establishing evidence of the bioavailability of certain formulations is general practice in the pharmaceutical industry.

The studies relevant for tacrolimus are non-randomized, cross-over studies, where each dog is it's own control. Four dogs, and four treatments are normally applied. As no iv injections are given, the bioavailabilities obtained are relative.

Further it has surprisingly been found that the need for simultaneous food intake in order to secure a sufficient uptake of tacrolimus is significantly reduced or even completely abolished.

Thus, the pharmaceutical compositions according to the invention provide significant higher bioavailability of tacrolimus, which may reduce the number of daily administered dosage units, and reduce or abolish the need for administration in connection with food intake, which provide for a higher degree of freedom for the recipient of the pharmaceutical compositions, and consequently the patients acceptance and/or compliance may be significantly improved. Furthermore, the compositions provide a significant reduction in side effects, especially side effect related to a high peak concentration (such as, e.g., nephro- and neuro-toxicity, diarrhea, constipation, abdominal pain, nausea etc) and provide for an extended release of tacrolimus leading to a better therapy.

As mentioned above, one of the major challenges with respect to formulation of tacrolimus compositions is to avoid an adverse food effect. In general, tacrolimus is much better absorbed when it is administered orally without food. A great variation in bioavailability is therefore seen following administration with or without food. This dependency makes it difficult to give precise guidelines as to how large a dose that should be administered and, furthermore, it requires information to the patient about the dosing regime. The present invention aims at providing compositions wherein the adverse food effect is reduced. Thus, the present invention provides a composition, which does not exhibit a significant adverse food effect after administration of the composition to a mammal in need of such a treatment as evidenced by a value of ($AUC_{fed}/AUC_{fasted}$) of at least about 0.85 with a lower 90% confidence limit of at least 0.75.

More specifically, a pharmaceutical composition according to the invention has a value of ($AUC_{fed}/AUC_{fasted}$) of about 0.9 or more such as, e.g., about 0.95 or more, about 0.97 or more or about 1 or more such as, e.g., up to about 1.1 or up to about 1.2.

A further advantage of a composition of the present invention is the possibility of obtaining an effective therapeutic response with a decreased dosage compared to traditional oral treatment. Accordingly, upon oral administration to a mammal in need thereof a pharmaceutical composition according to the invention releases tacrolimus or an analogue thereof in a controlled manner and the composition is essentially bioequivalent with Prograf® or a similar commercially available tacrolimus-containing product when administered in a dose that is at the about most about 85% w/w such as, e.g., at the most about 80% w/w, at the most about 75%, at the most about 70% w/w, at the most about 65% w/w, at the most about 60% w/w, at the most about 55% w/w or at the most about 50% w/w of the dose of tacrolimus administered in the form of Prograf® or a similar commercially available tacrolimus-containing product.

Parameters often used in bioequivalence studies are $t_{max}$, $C_{max}$, $AUC_{0\text{-}infinity}$, $AUC_{0\text{-}t}$. Other relevant parameters may be $W_{50}$, $W_{75}$ and/or MRT. Accordingly, at least one of these parameters may be applied when determining whether bioequivalence is present. Furthermore, in the present context, two compositions are regarded as bioequivalent if value of the parameter used is within 80-125% of that of Prograf® or a similar commercially available tacrolimus-containing product used in the test.

In the present context "$t_{max}$" denotes the time to reach the maximal plasma concentration ($c_{max}$) after administration; $AUC_{0\text{-}infinity}$ denotes the area under the plasma concentration versus time curve from time 0 to infinity; $AUC_{0\text{-}t}$ denotes the area under the plasma concentration versus time curve from time 0 to time t; $W_{50}$ denotes the time where the plasma concentration is 50% or more of $C_{max}$; $W_{75}$ denotes the time where the plasma concentration is 75% or more of $C_{max}$; and MRT denotes mean residence time for tacrolimus (and/or an analogue thereof).

Two other main disadvantages associated with treatment or prophylaxis with tacrolimus is the relative high incidence of side effects and a relatively high inter-individual variation. It is envisaged that a composition according to the invention will lead to a reduction in side effects. The reduction may be in terms of reduced frequency or in terms of severity. The side effects in question include e.g. nephro- and neuro-toxicity, diarrhea, constipation, abdominal pain, nausea etc. In one aspect the invention concerns a pharmaceutical composition in particulate form comprising tacrolimus or an analogue thereof together with one or more pharmaceutically acceptable excipient, wherein the composition upon oral administration to a mammal in need thereof releases tacrolimus or an analogue thereof in a controlled manner and reduces side effects compared to those of Prograf® administered under the same conditions and in a dose that provides an equivalent therapeutic effect.

Increasing the bioavailability, the Area Under the Curve, will normally reduce the intra- and inter-variability related to absorption of a drug substance. This is particularly true; whenever the low and impaired bioavailability is a consequence of poor water solubility. It is contemplated that compositions according to the invention will provide a CV (Coefficient of Variation) on Area under Curve data that are significantly smaller than with Prograf® and like products.

As mentioned hereinbefore, one of the basic features of the present invention is that it is possible to obtain an improvement in the bioavailability by oral administration of a composition of the present invention. Normally, a low bioavailability of a drug substance after oral administration is a barrier for design of a controlled or modified release composition of the drug substance due to the fact that it is almost impossible to obtain effective drug levels over a prolonged period of time. However, with the present technology it is possible to obtain a significantly improved bioavailability and thereby possible to design controlled, modified or delayed release compositions.

Tacrolimus is extensively metabolized by the CYP3A4 isoenzyme in the gut wall and liver. Accordingly, a suitable controlled release composition may be a composition that is designed to release tacrolimus in a delayed manner so as to avoid or reduce the CYP3A4 metabolism in the gastrointestinal tract.

Delayed release is mainly brought about by some kind of enteric coating. Whereas semipermeable coating will show some kind of delayed release, it does not preciously enough "delay" release. Additionally it requires a certain amount of time to release the content. The coating sought for this invention, is a pH dependant coating. This type of coating is very resistant to release of drug until a certain pH is reached. Within very few ¹⁄₁₀'th of pH, the film alters properties and becomes permeable. Examples of pH-sensitive polymers, which are relatively insoluble and impermeable at the pH of the stomach, but which are more soluble and permeable at the pH of the small intestine and colon include, but not limited to polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

pH-sensitive polymers of specific interest include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

The release of the active substance from a composition having a delayed release coating could also be an enzymatic reaction, if for example Zein or mono/di-glyceride mixtures are employed as coating material.

Upon oral administration to a mammal, including a human, in need thereof, a controlled release pharmaceutical composition according to the present invention releases tacrolimus in such a manner that a plasma concentration of at least about 5 ng/ml such as, e.g., at least about 7.5 ng/ml or at least about 10 ng/ml for a time period of at least about 24 hours is obtained. In a specific aspect of the invention the difference between the peak plasma concentration and plasma concentration measured 24 hours after administration is at the most about 20 ng/ml such as, e.g., at the most about 10 ng/ml, at the most about 7.5 ng/ml or at the most about 5 ng/ml.

In a specific aspect, the invention provides a pharmaceutical composition or a solid dosage form that releases tacrolimus and/or an analogue thereof relatively fast so as to enable a relatively fast onset of therapeutic effect. In one aspect, the invention relates to a pharmaceutical composition in particulate form comprising tacrolimus and/or an analogue thereof together with one or more pharmaceutically acceptable excipient, wherein the composition upon oral administration to a mammal in need thereof in a controlled manner releases at least about 50% w/w of the total amount of tacrolimus or an analogue thereof within about 24 hours, such as, e.g., within about 22 hours, within about 20 hours, within about 18 hours, within about 15 hours or within about 12 hours.

In a further embodiment at the most about 60% w/w such as, e.g., at the most 62% w/w, at the most about 65% w/w or at the most about 70% w/w tacrolimus is released 15 hours after oral administration to a mammal of a composition according to the invention or, alternatively, when tested in a suitable in vitro dissolution test, 15 hours after start of such a test.

More specifically, upon oral administration to a mammal in need thereof a composition according to the invention releases at least about 50% w/w of the total amount of tacrolimus and/or an analogue thereof within about 10 hours such as, e.g., within about 8 hours, within about 6 hours, within about 4 hours or within about 3 hours.

In another embodiment, upon oral administration to a mammal in need thereof, a pharmaceutical composition according to the invention releases at least 80% w/w tacrolimus after about 0.5 hours or more such as, e.g., after about 0.75 hours or more, about 1 hour or more, about 2 hours or more, about 3 hours or more, about 4 hours or more or about 5 hours or more; or alternatively, when tested in a suitable in vitro dissolution test releases at least 80% w/w after about 0.5 hours or more such as, e.g., after about 0.75 hours or more, about 1 hour or more, about 2 hours or more, about 3 hours or more, about 4 hours or more or about 5 hours or more after start of the test.

In a further embodiment, upon oral administration to a mammal in need thereof a pharmaceutical composition according to the invention releases at least about 55% w/w such as, e.g., about 60% w/w or more, about 65% w/w or more, about 70% w/w or more, about 75% w/w or more or about 80% w/w or more of the total amount of tacrolimus and/or an analogue thereof within about 24 hours, such as, e.g., within about 22 hours, within about 20 hours, within about 18 hours, about 15 hours, within about 12 hours, within about 10 hours, within 8 hours or within about 6 hours.

Furthermore or alternatively, at least about 50% w/w of the total amount of tacrolimus and/or an analogue thereof is released about 24 hours, within about 22 hours, within about 20 hours, within about 18 hours, within 15 hours, within about 12 hours, when tested in an in vitro dissolution test and employing a dissolution medium comprising a buffer having pH 7.5. Guidance for a suitable dissolution test is described in the Examples herein, but variations with respect to the specific method employed and the ingredients contained in the dissolution medium etc. are within the scope of the present invention. A person skilled in the art will know how to carry out a suitable dissolution test e.g. with guidance from USP, Ph.Eur. and the like. Suitable conditions for the in vitro dissolution test are employing USP dissolution test (paddle method) and a buffer pH 7.5 containing 2.5% SDS and 1 g/mL of pancreatin as dissolution medium.

In other embodiments, the following conditions are fulfilled with respect to in vitro dissolution test:

i) at least about 50% w/w of the total amount of tacrolimus or an analogue thereof is released within about 10 hours such as, e.g., within about 8 hours, within about 6 hours, within about 4 hours, within about 3 hours, within about 2 hours, within about 1 hour, within about 45 min, within about 30 min or within about 15 min, when tested in an in vitro dissolution test and employing a dissolution medium comprising a buffer having pH 7.5 ii) at least about 50% w/w of the total amount of tacrolimus or an analogue thereof is released within about 1.5 hours such as, e.g., within about 1 hour, within about 0.75 hours, within about 0.5 hours or within about 20 minutes, when tested in an in vitro dissolution test and employing a dissolution medium comprising a buffer having pH 7.5.

iii) at least about 55% w/w such as, e.g., about 60% w/w or more, about 65% w/w or more, about 70% w/w or more, about 75% w/w or more or about 80% w/w or more of the total amount of tacrolimus or an analogue thereof is released within about 15 hours such as, e.g., within about 12 hours, within about 10 hours, within 8 hours or within about 6 hours, when tested in an in vitro dissolution test and employing a dissolution medium comprising a buffer having pH 7.5 iv) at least about 55% w/w such as, e.g., about 60% w/w or more, about 65% w/w or more, about 70% w/w or more, about 75% w/w or more or about 80% w/w or more of the total amount of tacrolimus or an analogue thereof is released within about 5 hours such as, e.g., within about 4 hours, within about 3 hours, within about 2 hours, within about 1 hours or within about 30 minutes, when tested in an in vitro dissolution test and employing a dissolution medium comprising a buffer having pH 7.5, and/or v) at least about 20% w/w such as, e.g., at least about 25% w/w, at least about 30% w/w, at least about 35% w/w or at least about 40% w/w of the total amount of tacrolimus or an analogue thereof is released within the first 3 hours such as, e.g., within the first 2 hours or within the first hour when tested in an in vitro dissolution test and employing a dissolution medium comprising a buffer having pH 7.5.

In an interesting embodiment, the composition is designed to have a delayed release of tacrolimus and/or an analogue thereof. Therefore, the invention also includes a pharmaceutical composition in particulate form comprising tacrolimus and/or an analogue thereof together with one or more pharmaceutically acceptable excipient, wherein the composition upon oral administration to a mammal in need thereof has a delayed release of tacrolimus and/or an analogue thereof so that at the most 10% w/w such as, e.g., at the most about 7.5% w/w or at the most about 5% w/w of the total amount of tacrolimus or an analogue thereof is released within the first two hours such as, e.g., within the first hour after administration.

In other embodiments, the following conditions are fulfilled with respect to in vitro dissolution test performed under acidic conditions:

i) at the most about 30% w/w such as, e.g., at the most about 25% w/w, at the most about 20% w/w, at the most about 15% w/w or at the most about 10% w/w of tacrolimus or an analogue thereof is released within 2 hours in an in vitro dissolution test employing a dissolution medium having a pH of at the most about 5 such as, e.g. at the most about 4.5, at the most about 4, at the most about 3.5, at the most about 3, at the most about 2 or at the most about 1.5;

ii) at the most about 10% w/w such as, e.g., at the most about 7.5% w/w, at the most about 5% w/w or at the most about 2.5% w/w of tacrolimus or an analogue thereof is released within 2 hours in an in vitro dissolution test employing a dissolution medium having a pH of at the most about 5 such as, e.g. at the most about 4.5, at the most about 4, at the most about 3.5, at the most about 3, at the most about 2 or at the most about 1.5;

iii) at the most about 60% w/w such as, e.g., at the most about 50% w/w, at the most about 40% w/w or at the most about 30% w/w of tacrolimus or an analogue thereof is released within 15 hours such as, e.g., within about 12 hours, when tested in an in vitro dissolution test employing a dissolution medium having a pH of at the most about 4.5 such as, e.g. at the most about 4.0, at the most about 3.5, at the most about 3, at the most about 2 or at the most about 1.5;

iv) at the most about 40% w/w such as, e.g., at the most about 30% w/w, at the most about 25% w/w or at the most about 20% w/w of tacrolimus or an analogue thereof is released within 6 hours when tested in an in vitro dissolution test employing a dissolution medium having a pH of at the most about 4.5 such as, e.g. at the most about 4.0, at the most about 3.5, at the most about 3, at the most about 2 or at the most about 1.5, and/or v) at the most about 30% w/w such as, e.g., at the most about 25% w/w, at the most about 20% w/w or at the most about 15% w/w of tacrolimus or an analogue thereof is released within 4 hours when tested in an in vitro dissolution test employing a dissolution medium having a pH of at the most about 4.5 such as, e.g. at the most about 4.0, at the most about 3.5, at the most about 3, at the most about 2 or at the most about 1.5.

Apart from tacrolimus, a composition of the invention may also comprise a further therapeutically, prophylactically and/or diagnostically active substance. Notably combinations of tacrolimus with at least one of the following active substances are of interest: Substances that are indicated for use in connection with organ transplantation such as, e.g., steroids, calcineurin inhibitors and/or anti-proliferative agents. Specific examples include prednisone, prednisolone, methylprednisone, cyclosporin, mycophenolate, azathioprine, sirolimus, everolimus, mycophenolate sodium, and FTY720 (Novartis).

The pharmaceutical compositions may be prepared by any convenient method such as, e.g. granulation, mixing, spray drying etc. A particularly useful method is the method described in WO 03/004001. Herein is described a process for the preparation of particulate material by a controlled agglomeration method, i.e. a method, which enables a controlled growth in particle size. The method involves spraying a first composition comprising e.g. tacrolimus and a carrier, which has been melted, onto a second solid carrier medium. Normally, the meltable carrier has a melting point of at least 5° C. but lower than the melting point of tacrolimus. The melting point of the carrier may be in the range of 10° C. to 150° C., such as, e.g., in the range of 30° C. to 100° C. or in the range of 40° C. to 50° C. is most preferred.

It is within the skills of the average practitioner to select a suitable carrier being pharmaceutical acceptable, capable of dissolving or at least partly dissolve tacrolimus and having a melting point in the desired range using general knowledge and routine experimentation. Suitable candidate for carriers are described in WO 03/004001, which is herein incorporated by reference.

In the present context, suitable carriers are e.g. those mentioned as an oil or an oily-like material (as discussed later herein) as well as those disclosed in WO 03/004001. An advantage of using the controlled agglomeration method described in WO 03/004001 is that it is possible to apply a relatively large amount of a melt to a particulate material without having an undesirable growth in particle size. Accordingly, in one embodiment of the invention, the particulate material of a pharmaceutical composition has a geometric weight mean diameter $d_{gw}$ of ≥10 μm such as, e.g. ≥20 μm, from about 20 to about 2000, from about 30 to about 2000, from about 50 to about 2000, from about 60 to about 2000, from about 75 to about 2000 such as, e.g. from about 100 to about 1500 μm, from about 100 to about 1000 μm or from about 100 to about 700 μm, or at the most about 400 μm or at the most 300 μm such as, e.g., from about 50 to about 400 μm such as, e.g., from about 50 to about 350 μm, from about 50 to about 300 μm, from about 50 to about 250 μm or from about 100 to about 300 μm.

The particulate material obtained by the above-mentioned method has suitable properties with respect to flowability and/or compressibility and is therefore suitable for further processing into pharmaceutical dosage forms.

Solid Dispersion and/or Solid Solution of Tacrolimus

The solid dispersion or solid dispersion used in a preferred embodiment of the invention comprises an active ingredient selected among tacrolimus and analogues thereof, which ingredient is dispersed or dissolved in a hydrophilic or water-miscible vehicle having a melting point (freezing point or pour point) of at least 20° C. in a concentration of between about 0.01 w/w % and about 15 w/w %, and which dispersion is forming a solid dispersion or solid solution at ambient temperature (room temperature).

The concentration of the active ingredient in the hydrophilic or water-miscible vehicle is at the most 15 w/w %, preferably at the most 10 w/w %, preferably at the most 8 w/w %, more preferably at the most 6 w/w %, even more preferably at the most 5 w/w %, at the most 4% w/w, especially at the most 3 w/w %, in particular at the most 2% w/w; and/or is at least about 0.05 w/w %, preferably at least about 0.1 w/w %, more preferably at least about 0.5 w/w %, especially at least about 0.7 w/w %, in particular at least about 1 w/w %.

Physically, the combination of active ingredient and vehicle may either form a solid dispersion, i.e. the active ingredient is dispersed in the vehicle in particulate form, or may form a solid solution, i.e. the active ingredient is dissolved in the vehicle at a molecular level. The active ingredient and the vehicle may also form a solid dispersion having therein a part of the active ingredient dissolved at a molecular level. The physical state of the dispersion and/or solution may be determined by using various techniques such as Hot Stage Microscopy (HSM), Differential Scanning calorimetry (DSC), Scanning Electron Microscopy (SEM) optionally in combination with Energy Dispersive X-ray (EDX), and X-ray powder diffraction. In a preferred embodiment, the active ingredient is fully dissolved in the vehicle to form a solid solution at ambient temperature.

The solid dispersion of the invention exhibits a very fast immediate release of tacrolimus, when a composition comprising the dispersion or solution is tested in a dissolution test according to USP using an aqueous dissolution medium, and at least 50 w/w % of the active pharmaceutical ingredient is released within about 30 minutes, preferably within 20 minutes, more preferably within 15 minutes; such as at least 75 w/w % of the active pharmaceutical ingredient is released within about 40 minutes, or even better at least 90 w/w % of the active pharmaceutical ingredient is released within about 60 minutes, preferably within 45 minutes. For example, the test may be carried out according to the any method and any specifications cited in USP. Thus, the dissolution test may be carried out in an aqueous dissolution medium at a neutral or near-neutral pH, for example at pH 6.8, or at any acidic pH simulating the pH conditions in the gastrointestinal tract. However, variations with respect to the specific method employed and the ingredients contained in the dissolution medium etc. are within the scope of the present invention. A person skilled in the art will know how to carry out a suitable dissolution test e.g. with guidance from USP, Ph.Eur. and the like. Suitable conditions for the in vitro dissolution test are employing USP dissolution test (paddle method) and a buffer pH 7.5 containing 2.5% SDS and 1 g/mL of pancreatin as dissolution medium.

The hydrophilic or water-miscible vehicle to be used according to the invention is preferably one having a melting point (freezing point or pour point) of at least 20° C., more preferably at least 30° C., more preferably at least 40° C., more preferably at least 50° C., even more preferably at least 52° C., even more preferably at least 55° C., even more preferably at least 59° C., especially at least 61° C., in particular at least 65° C.

Examples of useful hydrophilic or water-miscible vehicles to be used according to this invention are selected from the group consisting of polyethylene glycols, polyoxyethylene oxides, poloxamers, polyoxyethylene stearates, poly-epsilon caprolactone, polyglycolized glycerides such as Gelucire®, and mixtures thereof.

In a preferred embodiment of the invention, the vehicle is a polyethylene glycol (PEG), in particular a PEG having an average molecular weight of at least 1500, preferably at least 3000, more preferably at least 4000, especially at least 6000. The polyethylene glycol may advantageously be mixed with one or more other hydrophilic or water-miscible vehicles, for example a poloxamer, preferably in a proportion (on a weight/weight basis) of between 1:3 and 10:1, preferably between 1:1 and 5:1, more preferably between and 3:2 4:1, especially between 2:1 and 3:1, in particular about 7:3. A specific example of a useful mixture is a mixture of PEG6000 and poloxamer 188 in the ratio 7:3.

For polyethylene glycols (PEG), the melting point (freezing point or pour point) increases as the average molecular weight increases. For example, PEG 400 is in the range of 4-8° C., PEG 600 is in the range of 20-25° C., PEG1500 is in the range of 44-48° C., PEG2000 is about 52° C., PEG 4000 is about 59° C., PEG 6000 is about 65° C. and PEG 8000 is about 61° C.

Useful poloxamers (also denoted polyoxypropylene-polyoxyethylene block copolymers) are for example poloxamer 188, poloxamer 237, poloxamer 338 or poloxamer 407 or other block copolymers of ethylene oxide and propylene oxide such as the Pluronic® and/or Tetronic® series. Suitable block copolymers of the Pluronic® series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic® F38, P65, P68LF, P75, F77, P84, P85, F87, F88, F98, P103, P104, P105, F108, P123, F123, F127, 10R8, 17R8, 25R5, 25R8 etc. Suitable block copolymers of the Tetronic® series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature.

In a preferred embodiment of the present invention, the poloxamer is poloxamer 188, which has an average molecular weight of about 8400 and a melting point of about 50-54° C.

Other useful hydrophilic or water-miscible vehicles may be polyvinylpyrrolidones, polyvinyl-polyvinylacetate copolymers (PVP-PVA), polyvinyl alcohol (PVA), polymethacrylic polymers (Eudragit RS; Eudragit RL, Eudragit NE, Eudragit E), cellulose derivatives including hydroxypropyl methylcellulose (HPMC), hydroxypropyl cellulose (HPC), methylcellulose, sodium carboxymethylcellulose, hydroxyethyl cellulose, pectins, cyclodextrins, galactomannans, alginates, carragenates, xanthan gums and mixtures thereof.

"Polyglycolized glycerides" denotes a mixture of mono-, di- and triglycerides and polyethylene glycol (PEG) mono- and diesters, preferably of molecular weight between 200 and 600, where appropriate of free glycerol and free PEG, whose HLB value is adjusted by the length of the PEG chain, and whose melting point is adjusted by the length of the chains of the fatty acids, of the PEG and by the degree of saturation of the fatty chains, and hence of the starting oil; examples of such mixtures are Gelucire®. Gelucire® compositions are inert semi-solid waxy materials which are amphiphilic in character and are available with varying physical characteristics. They are surface active in nature and disperse or solubilize in aqueous media forming micelles, microscopic globules or vesicles. They are identified by their melting point/HLB value. The melting point is expressed in degrees Celsius and the HLB (Hydrophile-Lipophile Balance) is a numerical scale extending from 0 to approximately 20. Lower HLB values denote more lipophilic and hydrophobic substances, and higher values denote more hydrophilic and lipophobic substances. The affinity of a compound for water or for oily substances is determined and its HLB value is assigned experimentally. One or a mixture of different grades of Gelucire® excipient may be chosen to achieve the desired characteristics of melting point and/or HLB value. They are mixtures of monoesters, diesters and/or triesters of glycerides of long chain ($C_{12}$ to $C_{18}$) fatty acids, and PEG (mono- and/or di) esters of long chain ($C_{12}$ to $C_{18}$) fatty acids and can include free PEG. Gelucire® compositions are generally described as fatty acid esters of glycerol and PEG esters or as polyglycolized glycerides. Gelucire® compositions are characterized by a wide range of melting points of from about 33° C. to about 64° C. and most commonly from about 35° C. to about 55° C., and by a variety of HLB values of from about 1 to about 14, most commonly from about 7 to about 14. For example, Gelucire® 50/13 designates a melting point of approximately 50° C. and an HLB value of about 13 to this grade of Gelucire®.

Pharmaceutically Acceptable Excipients

Examples of suitable excipients for use in a composition or solid dosage form according to the present invention include fillers, diluents, disintegrants, binders, lubricants and the like and mixtures thereof. As the composition or solid dosage form according to the invention may be used for different purposes, the choice of excipients is normally made taken such different uses into considerations. Other pharmaceutically acceptable excipients for suitable use are e.g. acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents and the like.

Examples of suitable fillers, diluents and/or binders include lactose (e.g. spray-dried lactose, α-lactose, β-lactose, Tabletose®, various grades of Pharmatose®, Microtose® or Fast-Floc®), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Specific examples of diluents are e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants are e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, carboxymethyl starch (e.g. Primogel® and Explotab®) etc.

Specific examples of binders are e.g. acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch etc.

Glidants and lubricants may also be included in the composition. Examples include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients which may be included in a composition or solid dosage form of the invention are e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

Other additives in a composition or a solid dosage form according to the invention may be antioxidants like e.g. ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, TPGS or other tocopherol derivatives, etc. The carrier composition may also contain e.g. stabilising agents. The concentration of an antioxidant and/or a stabilizing agent in the carrier composition is normally from about 0.1% w/w to about 5% w/w.

A composition or solid dosage form according to the invention may also include one or more surfactants or substances having surface-active properties. It is contemplated that such substances are involved in the wetting of the slightly soluble active substance and thus, contributes to improved solubility characteristics of the active substance.

Suitable excipients for use in a composition or a solid dosage form according to the invention are surfactants such as, e.g., amphiphilic surfactants as those disclosed in WO 00/50007 in the name of Lipocine, Inc. Examples of suitable surfactants are i) polyethoxylated fatty acids such as, e.g. fatty acid mono- or diesters of polyethylene glycol or mixtures thereof such as, e.g. mono- or diesters of polyethylene glycol with lauric acid, oleic acid, stearic acid, myristic acid, ricinoleic acid, and the polyethylene glycol may be selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, ii) polyethylene glycol glycerol fatty acid esters, i.e. esters like the above-mentioned but in the form of glyceryl esters of the individual fatty acids;

iii) glycerol, propylene glycol, ethylene glycol, PEG or sorbitol esters with e.g. vegetable oils like e.g. hydrogenated castor oil, almond oil, palm kernel oil, castor oil, apricot kernel oil, olive oil, peanut oil, hydrogenated palm kernel oil and the like, iv) polyglycerized fatty acids like e.g. polyglycerol stearate, polyglycerol oleate, polyglycerol ricinoleate, polyglycerol linoleate, v) propylene glycol fatty acid esters such as, e.g. propylene glycol monolaurate, propylene glycol ricinoleate and the like, vi) mono- and diglycerides like e.g. glyceryl monooleate, glyceryl dioleate, glyceryl mono- and/or dioleate, glyceryl caprylate, glyceryl caprate etc.;

vii) sterol and sterol derivatives;

viii) polyethylene glycol sorbitan fatty acid esters (PEG-sorbitan fatty acid esters) such as esters of PEG with the various molecular weights indicated above, and the various Tween® series;

ix) polyethylene glycol alkyl ethers such as, e.g. PEG oleyl ether and PEG lauryl ether;

x) sugar esters like e.g. sucrose monopalmitate and sucrose monolaurate;

xi) polyethylene glycol alkyl phenols like e.g. the Triton® X or N series;
xii) polyoxyethylene-polyoxypropylene block copolymers such as, e.g., the Pluronic® series, the Synperonic® series, Emkalyx®, Lutrol®, Supronic® etc. The generic term for these polymers is "poloxamers" and relevant examples in the present context are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407;
xiii) sorbitan fatty acid esters like the Span® series or Ariacel® series such as, e.g. sorbinan monolaurate, sorbitan monopalmitate, sorbitan monooleate, sorbitan monostearate etc.;
xiv) lower alcohol fatty acid esters like e.g. oleate, isopropyl myristate, isopropyl palmitate etc.;
xv) ionic surfactants including cationic, anionic and zwitterionic surfactants such as, e.g. fatty acid salts, bile salts, phospholipids, phosphoric acid esters, carboxylates, sulfates and sulfonates etc.

When a surfactant or a mixture of surfactants is present in a composition or a solid dosage form of the invention, the concentration of the surfactant(s) is normally in a range of from about 0.1-80% w/w such as, e.g., from about 0.1 to about 20% w/w, from about 0.1 to about 15% w/w, from about 0.5 to about 10% w/w, or alternatively, from about 0.10 to about 80% w/w such as, e.g. from about 10 to about 70% w/w, from about 20 to about 60% w/w or from about 30 to about 50% w/w.

In a specific aspect of the invention, the at least one of the one or more pharmaceutically acceptable excipient is selected from the group consisting of silica acid or a derivative or salt thereof including silicates, silicon dioxide and polymers thereof; magnesium aluminosilicate and/or magnesium aluminometasilicate, bentonite, kaolin, magnesium trisilicate, montmorillonite and/or saponite.

Such materials are is especially useful as a sorption material for oils or oily-like materials in pharmaceuticals, cosmetics and/or foodstuff. In a specific embodiment, the material is used as a sorption material for oils or oily-like materials in pharmaceuticals. The material that has the ability to function as a sorption material for oils or oily-like materials is also denoted "oil sorption material". Furthermore, in the present context the term "sorption" is used to denote "absorption" as well as "adsorption". It should be understood that whenever one of the terms is used it is intended to cover the phenomenon absorption as well as adsorption.

Notably, the pharmaceutically acceptable excipient may comprise a silica acid or a derivative or salt thereof such as, e.g., silicon dioxide or a polymer thereof as a pharmaceutically acceptable excipient. Dependent on the quality employed a silicon dioxide may be a lubricant or it may be an oil sorption material. Qualities fulfilling the latter function seem to be most important.

In a specific embodiment, a composition or solid dosage form according to invention comprises a pharmaceutically acceptable excipient that is a silicon dioxide product that has properties corresponding to Aeroperl® 300 (available from Degussa, Frankfurt, Germany). As it appears from the examples herein, a very suitable material is Aeroperl® 300 (including materials with properties like or corresponding to those of Aeroperl® 300).

Use of an oil sorption material in compositions or dosage forms according to the invention is very advantageous for the preparation of pharmaceutical, cosmetic, nutritional and/or food compositions, wherein the composition comprises oil or an oily-like material. One of the advantages is that is it possible to incorporate a relatively large amount of oil and oily-like material and still have a material that is solid. Thus, it is possible to prepare solid compositions with a relatively high load of oil or oily-like materials by use of an oil sorption material according to the invention. Within the pharmaceutical field it is an advantage to be able to incorporate a relatively large amount of an oil or an oily-like material in a solid composition especially in those situation where the active substance does not have suitable properties with respect to water solubility (e.g. poor water solubility), stability in aqueous medium (i.e. degradation occurs in aqueous medium), oral bioavailability (e.g. low bioavailability) etc., or in those situations where it is desired to modify the release of an active substance from a composition in order to obtain a controlled, delayed, sustained and/or pulsed delivery of the active substance. Thus, in a specific embodiment it is used in the preparation of pharmaceutical compositions.

The oil sorption material for use in the processing into solid compositions normally absorbs about 5% w/w or more, such as, e.g., about 10% w/w or more, about 15% w/w or more, about 20% w/w or more, about 25% w/w or more, about 30% w/w or more, about 35% w/w or more, about 40% w/w or more, about 45% w/w or more, about 50 w/w or more, about 55% w/w or more, about 60% w/w or more, about 65% w/w or more, about 70% w/w or more, about 75% w/w or more, about 80% w/w or more, about 85% w/w or more, about 90% w/w or more or about 95% w/w or more of an oil or an oily material and is still a solid material.

Yet another aspect of the invention relates to compositions or solid dosage forms comprising an oil or an oily material.

In the present context the term "oils and oily materials" is used in a very broad sense including oils, waxes, semi-solid materials and materials that normally are used as solvents (such as organic solvents) or cosolvents within the pharmaceutical industry, and the term also includes therapeutically and/or prophylactically active substances that are in liquid form at ambient temperature; furthermore the term includes emulsions like e.g. microemulsions and nanoemulsions and suspensions. The oils and oily-like materials that can be absorbed will normally be liquid at ambient or elevated temperature (for practical reasons the max. temperature is about 250° C.). They may be hydrophilic, lipophilic, hydrophobic and/or amphiphilic materials.

The oils and oily-like material that are suitable for use in the present context are substances or materials, which have a melting point of at least about 0° C. and at the most about 250° C.

In specific embodiments of the invention, the oil or oily-like material has a melting point of about 5° C. or more such as, e.g., about 10° C. or more, about 15° C. or more, about 20° C. or more or about 25° C. or more.

In further embodiments of the invention, the oil or oily-like material has a melting point of at least about 25° C. such as, e.g., at least about 30° C. at least about 35° C. or at least about 40° C. For practical reasons, the melting point may normally not be too high, thus, the oil or oily-like material normally has a melting point of at the most about 300° C. such as, e.g., at the most about 250° C., at the most about 200° C., at the most about 150° C. or at the most about 100° C. If the melting point is higher a relatively high temperature may promote e.g. oxidation or other kind of degradation of an active substance in those cases where e.g. a therapeutically and/or prophylactically active substance is included.

In the present context, the melting point is determined by DSC (Differential Scanning calorimetry). The melting point is determined as the temperature at which the linear increase of the DSC curve intersects the temperature axis.

Interesting oils or oily-like materials are generally substances, which are used in the manufacture of pharmaceuticals as so-called melt binders or solid solvents (in the form of solid dosage form), or as co-solvents or ingredients in pharmaceuticals for topical use.

It may be hydrophilic, hydrophobic and/or have surface-active properties. In general hydrophilic and/or hydrophobic oils or oily-like materials are suitable for use in the manufacture of a pharmaceutical composition comprising a therapeutically and/or prophylactically active substance that has a relatively low aqueous solubility and/or when the release of the active substance from the pharmaceutical composition is designed to be immediate or non-modified. Hydrophobic oil or oily-like materials, on the other hand, are normally used in the manufacture of a modified release pharmaceutical composition. The above-given considerations are simplified to illustrate general principles, but there are many cases where other combinations of oils or oily-like materials and other purposes are relevant and, therefore, the examples above should not in any way limit the invention.

Typically, a suitable hydrophilic oil or oily-like material is selected from the group consisting of: polyether glycols such as, e.g., polyethylene glycols, polypropylene glycols; polyoxyethylenes; polyoxypropylenes; poloxamers and mixtures thereof, or it may be selected from the group consisting of: xylitol, sorbitol, potassium sodium tartrate, sucrose tribehenate, glucose, rhamnose, lactitol, behenic acid, hydroquinon monomethyl ether, sodium acetate, ethyl fumarate, myristic acid, citric acid, Gelucire 50/13, other Gelucire types such as, e.g., Gelucire 44/14 etc., Gelucire 50/10, Gelucire 62/05, Sucro-ester 7, Sucro-ester 11, Sucro-ester 15, maltose, mannitol and mixtures thereof.

A suitable hydrophobic oil or oily-like material may be selected from the group consisting of: straight chain saturated hydrocarbons, sorbitan esters, paraffins; fats and oils such as e.g., cacao butter, beef tallow, lard, polyether glycol esters; higher fatty acid such as, e.g. stearic acid, myristic acid, palmitic acid, higher alcohols such as, e.g., cetanol, stearyl alcohol, low melting point waxes such as, e.g., glyceryl monostearate, glyceryl monooleate, hydrogenated tallow, myristyl alcohol, stearyl alcohol, substituted and/or unsubstituted monoglycerides, substituted and/or unsubstituted diglycerides, substituted and/or unsubstituted triglycerides, yellow beeswax, white beeswax, carnauba wax, castor wax, japan wax, acetylate monoglycerides; NVP polymers, PVP polymers, acrylic polymers, or a mixture thereof.

In an interesting embodiment, the oil or oily-like material is a polyethylene glycol having an average molecular weight in a range of from about 400 to about 35,000 such as, e.g., from about 800 to about 35,000, from about 1,000 to about 35,000 such as, e.g., polyethylene glycol 1,000, polyethylene glycol 2,000, polyethylene glycol 3,000, polyethylene glycol 4,000, polyethylene glycol 5,000, polyethylene glycol 6000, polyethylene glycol 7,000, polyethylene glycol 8,000, polyethylene glycol 9,000 polyethylene glycol 10,000, polyethylene glycol 15,000, polyethylene glycol 20,000, or polyethylene glycol 35,000. In certain situations polyethylene glycol may be employed with a molecular weight from about 35,000 to about 100,000.

In another interesting embodiment, the oil or oily-like material is polyethylene oxide having a molecular weight of from about 2,000 to about 7,000,000 such as, e.g. from about 2,000 to about 100,000, from about 5,000 to about 75,000, from about 10,000 to about 60,000, from about 15,000 to about 50,000, from about 20,000 to about 40,000, from about 100,000 to about 7,000,000 such as, e.g., from about 100,000 to about 1,000,000, from about 100,000 to about 600,000, from about 100,000 to about 400,000 or from about 100,000 to about 300,000.

In another embodiment, the oil or oily-like material is a poloxamer such as, e.g. Poloxamer 188, Poloxamer 237, Poloxamer 338 or Poloxamer 407 or other block copolymers of ethylene oxide and propylene oxide such as the Pluronic® and/or Tetronic® series. Suitable block copolymers of the Pluronic® series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic® F38, P65, P68LF, P75, F77, P84, P85, F87, F88, F98, P103, P104, P105, F108, P123, F123, F127, 10R8, 17R8, 25R5, 25R8 etc. Suitable block copolymers of the Tetronic® series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature.

The oil or oily-like material may also be a sorbitan ester such as, e.g., sorbitan di-isostearate, sorbitan dioleate, sorbitan monolaurate, sorbitan monoisostearate, sorbitan monooleate, sorbitan monopalmitate, sorbitan monostearate, sorbitan sesqui-isostearate, sorbitan sesquioleate, sorbitan sesquistearate, sorbitan tri-isostearate, sorbitan trioleate, sorbitan tristearate or mixtures thereof.

The oil or oily-like material may of course comprise a mixture of different oils or oily-like materials such as, e.g., a mixture of hydrophilic and/or hydrophobic materials.

Other suitable oils or oily-like materials may be solvents or semi-solid excipients like, e.g. propylene glycol, polyglycolised glycerides including Gelucire 44/14, complex fatty materials of plant origin including theobroma oil, carnauba wax, vegetable oils like e.g. almond oil, coconut oil, corn oil, cottonseed oil, sesame oil, soya oil, olive oil, castor oil, palm kernels oil, peanut oil, rape oil, grape seed oil etc., hydrogenated vegetable oils such as, e.g. hydrogenated peanut oil, hydrogenated palm kernels oil, hydrogenated cottonseed oil, hydrogenated soya oil, hydrogenated castor oil, hydrogenated coconut oil; natural fatty materials of animal origin including beeswax, lanolin, fatty alcohols including cetyl, stearyl, lauric, myristic, palmitic, stearic fatty alcohols; esters including glycerol stearate, glycol stearate, ethyl oleate, isopropyl myristate; liquid interesterified semi-synthetic glycerides including Miglycol 810/812; amide or fatty acid alcolamides including stearamide ethanol, diethanolamide of fatty coconut acids, acetic acid esters of mono and di-glycerides, citric acid esters of mono and di-glycerides, lactic acid esters of mono and diglycerides, mono and di-glycerides, poly-glycerol esters of fatty acids, poly-glycerol poly-ricinoleate, propylene glycol esters of fatty acids, sorbitan monostearates, sorbitan tristearates, sodium stearoyl lactylates, calcium stearoyl lactylates, diacetyl tartaric acid esters of mono and di-glycerides etc.

Normally, a pharmaceutical composition or a solid dosage form according to the invention has a concentration of the oil or oily-like material in the composition of about 5% w/w or more such as, e.g., about 10% w/w or more, about 15% w/w or more, about 20% w/w or more, about 25% w/w or more, about 30% w/w or more, about 35% w/w or more, about 40% w/w or more, about 45% w/w or more, about 50 w/w or more, about 55% w/w or more, about 60% w/w or more, about 65% w/w or more, about 70% w/w or more, about 75% w/w or more, about 80% w/w or more, about 85% w/w or more, about 90% w/w or more about 95% w/w or more.

In specific embodiments the concentration of the oil or oily-like material in a composition or solid dosage form of the invention is in a range from about 20% to about 80% w/w such as, e.g., from about 25% to about 75% w/w.

One of the advantages is that is it possible to incorporate a relatively large amount of oil and oily-like material and still have a material that is solid. Thus, it is possible to prepare solid compositions with a relatively high load of oil or oily-like materials by use of an oil sorption material according to the invention. Within the pharmaceutical field it is an advantage to be able to incorporate a relatively large amount of an oil or an oily-like material in a solid composition especially in those situation where the active substance does not have suitable properties with respect to water solubility (e.g. poor water solubility), stability in aqueous medium (i.e. degradation occurs in aqueous medium), oral bioavailability (e.g. low bioavailability) etc., or in those situations where it is desired to modify the release of an active substance from a composition in order to obtain a controlled, delayed, sustained and/or pulsed delivery of the active substance.

A further advantage is that the particulate material obtained is a free-flowing powder and therefore readily processable into e.g. solid dosage forms such as tablets, capsules or sachets. Normally, the particulate material has properties that are suitable in order to manufacture tablets by direct compression without addition of large amounts of further additives. A suitable test for testing the flowability of the particulate material is the method described in Ph.Eur. and measuring the flow rate of the material out of a funnel with a nozzle (orifice) diameter of 10.0 mm.

In an important embodiment of the invention, at least a part of tacrolimus and/or an analogue thereof is present in the composition in the form of a solid solution including a molecular dispersion and a solid dispersion. Normally, 10% or more such as, e.g., 20% or more, 30% or more, 40% or more, 50% or more, 60% or more, 70% or more, 80% or more, 90% or more such as, e.g., 95% or more or about 100% w/w of tacrolimus and/or an analogue thereof is present in the composition in the form of a solid dispersion.

A solid dispersion may be obtained in different ways e.g. by employing organic solvents or by dispersing or dissolving the active substance in another suitable medium (e.g. an oil or an oily-like material that is in liquid form at room temperature or at elevated temperatures).

Solid dispersions (solvent method) may for example be prepared by dissolving a physical mixture of the active substance (e.g. a drug substance) and the carrier in a common organic solvent, followed by evaporation of the solvent. The carrier is often a hydrophilic polymer. Suitable organic solvents include pharmaceutical acceptable solvent in which the active substance is soluble such as methanol, ethanol, methylene chloride, chloroform, ethylacetate, acetone or mixtures thereof.

Suitable water soluble carriers include polymers such as polyethylene glycol, poloxamers, polyoxyethylene stearates, poly-ε-caprolactone, polyvinylpyrrolidone (PVP), polyvinylpyrrolidone-polyvinylacetate copolymer PVP-PVA (Kollidon VA64), poly-methacrylic polymers (Eudragit RS, Eudragit RL, Eudragit NE, Eudragit E) and polyvinyl alcohol (PVA), hydroxypropyl cellulose (HPC), hydroxypropyl methyl cellulose (HPMC), methyl cellulose, and poly(ethylene oxide) (PEO).

Polymers containing acidic functional groups may be suitable for solid dispersions, which release the active substance in a preferred pH range providing acceptable absorption in the intestines. Such polymers may be one or more selected from the group comprising hydroxypropyl methylcellulose phtalate (HMPCP), polyvinyl acetate phtalate (PVAP), hydroxypropylmethylcellulose acetate succinate (HPMCAS), alginate, carbomer, carboxymethylcellulose, methacrylic acid copolymer (Eudragit L, Eudragit S), shellac, cellulose acetate phthalate (CAP), starch glycolate, polacrylin, methyl cellulose acetate phtalate, hydroxypropyulcellulose acetate phthalate, cellulose acetate terephthalate, cellulose acetate isophthalate and cellulose acetate trimellitate.

Relative to the amount of the active substance and the polymer in the solid dispersion, the weight ratio of active substance to polymer may be in a range of from about 3:1 to about 1:20. However, narrower ranger of from about 3:1 to about 1:5, such as, e.g., from about 1:1 to about 1:3 or about may also be used.

The solid dispersion is preferably formed by spray drying techniques, controlled agglomeration, freeze-drying or coating on carrier particles or any other solvent removal process. The dried product contains the active substance present in the form of a solid dispersion including a molecular dispersion and a solid solution.

As an alternative to the use of organic solvents the drug and polymer may be co-grinded or extruded at elevated temperatures (melt extrusion).

The pharmaceutical compositions comprising tacrolimus at least partly in form of a solid dispersion or solution may in principle be prepared using any suitable procedure for preparing pharmaceutical compositions known within the art.

Apart from using the organic solvent based method, solid dispersion or solid solutions of tacrolimus and/or an analogue thereof may be obtained by dispersing and/or dissolving tacrolimus in the carrier composition used in the controlled agglomeration method. Stabilizing agents etc. may be added in order to ensure the stability of the solid dispersion/solution.

In another aspect, the invention relates to a method for the preparation of a pharmaceutical composition according to the invention. In general, any suitable method within the pharmaceutical field may be employed. However, in order to enable incorporation of a relatively high amount of an oil or an oily-like material especially the method described in WO 03/004001 has proved useful. WO 03/004001 is hereby incorporated by reference. The method comprises spraying a first composition in liquid form, said composition comprising a first vehicle or carrier and having a melting point above 5° C. onto a second composition comprising a second support or carrier material, said second composition e.g. being in the fluidised state and having a temperature below the melting point of the first vehicle or carrier. The active substance may be present in the first vehicle or carrier composition and/or in the second support or carrier composition. However, in those cases where tacrolimus and/or an analogue thereof are present, at least partly, in the form of as a solid dispersion, it is advantageous to incorporate or dissolve tacrolimus and/or an analogue thereof in the first vehicle or carrier composition.

Solid Dosage Forms

The pharmaceutical composition according to the invention is in particulate form and may be employed as such. However, in many cases it is more convenient to present the composition in the form of granules, pellets, microspheres, nanoparticles and the like or in the form of solid dosage forms including tablets, capsules and sachets and the like. A solid dosage form according to the invention may be a single unit dosage form or it may in the form of a polydepot dosage form contain a multiplicity of individual units such as, e.g., pellets, beads and/or granules.

Normally, a pharmaceutical composition or a solid dosage form of the invention is intended for administration via the oral, buccal or sublingual administration route.

The invention also relates to the above-mentioned presentation form. Within the scope of the invention are compositions/solid dosage forms that are intended to release tacrolimus and/or an analogue thereof in a fast release, a delayed release or modified release manner. All of these manners are considered to be a controlled manner. Further, a pH dependants release is also covered by the term "controlled manner".

A solid dosage form according to the present invention comprises a pharmaceutical composition in particulate form as described above. The details and particulars disclosed under this main aspect of the invention apply mutatis mutandis to the other aspects of the invention. Accordingly, the properties with respect to increase in bioavailability, changes in bioavailability parameters, reduction in adverse food effect as well as release of tacrolimus and/or an analogue thereof etc. described and/or claimed herein for pharmaceutical compositions in particulate form are analogues for a solid dosage form according to the present invention.

Normally, the concentration of the pharmaceutical composition in particulate form is in a range of from about 5 to 100% w/w such as, e.g., from about 10% to about 90% w/w, from about 15% to about 85% w/w, from about 20% to about 80% w/w, from about 25% to about 80% w/w, from about 30% to about 80% w/w, from about 35% to about 80% w/w, from about 40% to about 75% w/w, from about 45% to about 75% w/w or from about 50% to about 70% w/w of the dosage form. In an embodiment of the invention, the concentration of the pharmaceutical composition in particulate form is 50% w/w or more of the dosage form.

A solid dosage form according to the invention is obtained by processing the particulate material according to the invention by means of techniques well-known to a person skilled in the art. Normally, it involves further addition of one or more of the pharmaceutically acceptable excipients mentioned herein.

The composition or solid dosage form according to the invention may be designed to release tacrolimus and/or an analogue thereof in any suitable manner provided that the increase in bioavailability is present. Thus, the active substance may be released relatively fast in order to obtain an enhanced on-set of action, it may be released so as to follow zero or first order kinetics or it may be released in a modified manner in order to obtain a predetermined pattern of release. All of these ways are considered controlled manners. Plain formulations are also within the scope of the present invention.

The recommended dosage range for Prograf® is 0.1 to 0.2 mg/kg/day given every 12 hours in two divided doses. More importantly the blood levels has to be monitored.

The typical level for 1-3 months is 7-20 ng/mL and 4-12 months the levels should be 5-15 ng/mL. This is only guiding values and may vary from types of transplant and ethnicity.

The following was found for kidney transplant patients.

| Time After Transplant | Caucasian n = 114 | | Black n = 56 | |
|---|---|---|---|---|
| | Dose (mg/kg) | Trough Concentrations (ng/mL) | Dose (mg/kg) | Trough Concentrations (ng/mL) |
| Day 7 | 0.18 | 12.0 | 0.23 | 10.9 |
| Month 1 | 0.17 | 12.8 | 0.26 | 12.9 |
| Month 6 | 0.14 | 11.8 | 0.24 | 11.5 |
| Month 12 | 0.13 | 10.1 | 0.19 | 11.0 |

The expected dosage recommendation for products of the present invention will be from 0.02 mg/kg/day to 0.15 mg/kg/day, dosed once a day.

The composition or solid dosage form according to the invention may also be coated with a film coating, an enteric coating, a modified release coating, a protective coating, an anti-adhesive coating etc.

A solid dosage form according to the invention may also be coated in order to obtain suitable properties e.g. with respect to controlled release of the active substance. The coating may be applied on single unit dosage forms (e.g. tablets, capsules) or it may be applied on a polydepot dosage form or on its individual units.

Suitable coating materials are e.g. methylcellulose, hydroxypropylmethylcellulose, hydroxypropylcellulose, acrylic polymers, ethylcellulose, cellulose acetate phthalate, polyvinyl acetate phthalate, hydroxypropyl methylcellulose phthalate, polyvinylalcohol, sodium carboxymethylcellulose, cellulose acetate, cellulose acetate phthalate, gelatin, methacrylic acid copolymer, polyethylene glycol, shellac, sucrose, titanium dioxide, carnauba wax, microcrystalline wax, glyceryl monostearate, zein.

Plasticizers and other ingredients may be added in the coating material. The same or different active substance may also be added in the coating material.

In preferred embodiments of the invention, the solid dosage forms are designed to release tacrolimus and/or an analogue thereof in a controlled manner. In the present context, the term "controlled manner" is intended to include all types of release which differ from the release obtained from plain tablets. Thus, the term includes so-called "controlled release", "modified release", "sustained release", "pulsed release", "prolonged release", burst release", "slow release", "extended release", as well as the terms "delayed release" and pH dependant release. However, a specific aspect of the invention relates to a delayed release composition or dosage form, which in this context is intended to denote a composition or dosage form that at the most releases 10% w/w of the active substance within the first 2 hours after administration and/or after start of a dissolution test employing a dissolution medium having a pH of at the most about 3.

Modified Release Systems

A first modified release system includes matrix systems, in which tacrolimus is embedded or dispersed in a matrix of another material that serves to retard the release of tacrolimus into an aqueous environment (i.e., the luminal fluid of the GI tract). When tacrolimus is dispersed in a matrix of this sort, release of the drug takes place principally from the surface of the matrix. Thus the drug is released from the surface of a device, which incorporates the matrix after it diffuses through the matrix or when the surface of the device erodes, exposing the drug. In some embodiments, both mechanisms can operate simultaneously. The matrix systems may be large, i.e., tablet sized (about 1 cm), or small (<0.3 cm). The system may be unitary (e.g., a bolus), may be divided by virtue of being composed of several sub-units (for example, several capsules which constitute a single dose) which are administered substantially simultaneously, or may comprise a plurality of particles, also denoted a multiparticulate. A multiparticulate can have numerous formulation applications. For example, a multiparticulate may be used as a powder for filling a capsule shell, or used per se for mixing with food to ease the intake.

In a specific embodiment, a matrix multiparticulate, comprises a plurality of tacrolimus-containing particles, each particle comprising tacrolimus and/or an analogue thereof e.g. in the form of a solid solution/dispersion with one or more excipients selected to form a matrix capable of controlling the dissolution rate of the tacrolimus into an aqueous medium. The matrix materials useful for this embodiment are generally hydrophobic materials such as waxes, some cellulose derivatives, or other hydrophobic polymers. If needed, the matrix materials may optionally be formulated with hydrophobic materials, which can be used as binders or as enhancers. Matrix materials useful for the manufacture of these dosage forms include such as: ethylcellulose, waxes such as paraffin, modified vegetable oils, carnauba wax, hydrogenated castor oil, beeswax, and the like, as well as synthetic polymers such as poly(vinyl chloride), poly(vinyl acetate), copolymers of vinyl acetate and ethylene, polystyrene, and the like. Water soluble or hydrophilic binders or release modifying agents which can optionally be formulated into the matrix include hydrophilic polymers such as hydroxypropyl cellulose (HPC), hydroxypropyl methyl cellulose (HPMC), methyl cellulose, poly (N-vinyl-2-pyrrolidinone) (PVP), poly(ethylene oxide) (PEO), poly(vinyl alcohol) (PVA), xanthan gum, carrageenan, and other such natural and synthetic materials. In addition, materials, which function as release-modifying agents include water-soluble materials such as sugars or salts. Preferred water-soluble materials include lactose, sucrose, glucose, and mannitol, as well as hydrophillic polymers like e.g. HPC, HPMC, and PVP.

In a specific embodiment, a multiparticulate product is defined as being processed by controlled agglomeration. In this case tacrolimus is dissolved or partly dissolved in a suitable meltable carrier and sprayed on carrier particles comprising the matrix substance.
Suitable meltable carriers are mentioned previously herein.

Alternatively, tacrolimus is dissolved in an organic solvent together with the matrix substance and spray dried or applied to carrier particles, cf. below. Solvents typically employed for the process include acetone, ethanol, isopropanol, ethyl acetate, and mixtures of two or more.

Once formed, tacrolimus matrix multiparticulates may be blended with compressible excipients such as lactose, microcrystalline cellulose, dicalcium phosphate, and the like and the blend compressed to form a tablet. Disintegrants such as sodium starch glycolate or crosslinked poly(vinyl pyrrolidone) are also usefully employed. Tablets prepared by this method disintegrate when placed in an aqueous medium (such as the GI tract), thereby exposing the multiparticulate matrix, which releases tacrolimus therefrom.

In a further embodiment, the matrix system is in the form of a hydrophilic matrix tablet containing tacrolimus and/or an analogue thereof (e.g. in the form of a solid dispersion) as a multiparticulate product and an amount of hydrophilic polymer sufficient to provide a useful degree of control over the tacrolimus dissolution. Hydrophilic polymers useful for forming the matrix include hydroxypropylmethyl cellulose (HPMC), hydroxypropyl cellulose (HPC), poly (ethylene oxide), poly(vinyl alcohol), xanthan gum, carbomer, carrageenan, and zooglan. A preferred material is HPMC. Other similar hydrophilic polymers may also be employed. In use, the hydrophilic material is swollen by, and eventually dissolves in, water. The tacrolimus is released both by diffusion from the matrix and by erosion of the matrix. The tacrolimus dissolution rate of these hydrophilic matrix tablets may be controlled by the amount, molecular weight and gel strengths of the hydrophilic polymer employed. In general, using a greater amount of the hydrophilic polymer decreases the dissolution rate, as does using a higher molecular weight polymer. Using a lower molecular weight polymer normally increases the dissolution rate. A matrix tablet typically comprises about 20 to 90% by weight of tacrolimus and about 80 to 10% by weight of polymer.

A preferred matrix tablet comprises, by weight, about 30% to about 80% solid dispersion containing tacrolimus and/or an analogue thereof about 15% to about 35% matrix former (such as, e.g., HPMC), 0% to about 35% lactose, 0% to about 20% microcrystalline cellulose, and about 0.25% to about 2% lubricant (such as, e.g., magnesium stearate).

The matrix systems as a class often exhibit non-constant release of the drug from the matrix. This result may be a consequence of the diffusive mechanism of drug release, and modifications to the geometry of the dosage form can be used with advantage to make the release rate of the drug more constant.

A second class of tacrolimus controlled-release dosage forms of this invention includes membrane-moderated or reservoir systems. In this class, a reservoir of tacrolimus e.g. in a solid solution/dispersion as a multiparticulate product is surrounded by a rate-limiting membrane. The tacrolimus traverses the membrane by mass transport mechanisms well known in the art, including but not limited to dissolution in the membrane followed by diffusion across the membrane or diffusion through liquid-filled pores within the membrane. These individual reservoir system dosage forms may be large, as in the case of a tablet containing a single large reservoir, or multiparticulate, as in the case of a capsule or polydepot tablets containing a plurality of reservoir particles, each individually coated with a membrane. The coating can be non-porous, yet permeable to tacrolimus (for example tacrolimus may diffuse directly through the membrane), or it may be porous. As with other embodiments of this invention, the particular mechanism of transport is not believed to be critical.

Sustained release coatings as known in the art may be employed to fabricate the membrane, especially polymer coatings, such as a cellulose ester or ether, an acrylic polymer, or a mixture of polymers. Preferred materials include ethyl cellulose, cellulose acetate and cellulose acetate butyrate. The polymer may be applied as a solution in an organic solvent or as an aqueous dispersion or latex. The coating operation may be conducted in standard equipment such as a fluid bed coater, a Wurster coater, or a rotary fluid bed coater.

If desired, the permeability of the coating may be adjusted by blending of two or more materials. A particularly useful process for tailoring the porosity of the coating comprises adding a pre-determined amount of a finely-divided water-soluble material, such as sugars or salts or water-soluble polymers to a solution or dispersion (e.g., an aqueous latex) of the membrane-forming polymer to be used. When the dosage form is ingested into the aqueous medium of the GI tract, these water soluble membrane additives are leached out of the membrane, leaving pores which facilitate release of the drug. The membrane coating can also be modified by the addition of plasticizers, as known in the art.

A particularly useful variation of the process for applying a membrane coating comprises dissolving the coating polymer in a mixture of solvents chosen such that as the coating dries, a phase inversion takes place in the applied coating solution, resulting in a membrane with a porous structure.

In general, a support for mechanically strengthening the membrane is not required.

The morphology of the membrane is not of critical importance so long as the permeability characteristics enumerated herein are met. The membrane can be amorphous or crystalline. It can have any category of morphology produced by any particular process and can be, for example, an interfacially-polymerized membrane (which comprises a thin rate-limiting skin on a porous support), a porous hydrophilic membrane, a porous hydrophobic membrane, a hydrogel membrane, an ionic membrane, and other such materials which are characterized by controlled permeability to tacrolimus.

In one embodiment of the invention it is an aim to reduce the exposure of the upper GI tract to high concentrations of tacrolimus. Accordingly, suitable dosage forms includes those forms, which incorporate a specific delay before the onset of controlled release of tacrolimus. An exemplary embodiment can be illustrated by a tablet (or a particulate material) comprising a core containing tacrolimus coated with a first coating of a polymeric material of the type useful for sustained release of tacrolimus and a second coating of the type useful for delaying release of drugs when the dosage form is ingested. The first coating is applied over and surrounds the tablet or individual particles. The second coating is applied over and surrounds the first coating.

A tablet can be prepared by techniques well known in the art and contains a therapeutically useful amount of tacrolimus plus such excipients as are necessary to form the tablet by such techniques.

The first coating may be a sustained release coating as known in the art, especially polymer coatings, to fabricate the membrane, as previously discussed for reservoir systems. or it could be a controlled release matrix core, which are coated a second time with a delayed release material.

Materials useful for preparing the second coating on the tablet include polymers known in the art as enteric coatings for delayed-release of pharmaceuticals. These most commonly are pH-sensitive materials such as cellulose acetate phthalate, cellulose acetate trimellitate, hydroxypropyl methyl cellulose phthalate, poly (vinyl acetate phthalate), and acrylic copolymers such as Eudragit L-100 (Röhm Pharma) and related materials, as more fully detailed below under "Delayed Release". The thickness of the delayed-release coating is adjusted to give the desired delay property. In general, thicker coatings are more resistant to erosion and, consequently, yield a longer and more effective delay. Preferred coatings range from about 30 μm in thickness to about 3 mm in thickness.

When using a hydrophobic matrix material like glyceryl monostearate, no delay coating is necessary. The tablet will not release tacrolimus until an area of enzymatic degradation has been reached, more specifically after the duodenum.

When ingested, the twice-coated tablet passes through the stomach, where the second coating prevents release of the tacrolimus under the acidic conditions prevalent there. When the tablet passes out of the stomach and into the small intestine, where the pH is higher, the second coating erodes or dissolves according to the physicochemical properties of the chosen material. Upon erosion or dissolution of the second coating, the first coating prevents immediate or rapid release of the tacrolimus and modulates the release so as to prevent the production of high peak concentrations, thereby minimizing side-effects.

A further preferred embodiment comprises a multiparticulate wherein each particle is dual coated as described above for tablets, first with a polymer designed to yield sustained release of the tacrolimus and then coated with a polymer designed to delay onset of release in the environment of the GI tract when the dosage form is ingested.

The rate of tacrolimus release from the sustained-release-coated multiparticulates (i.e., the multiparticulates before they receive the delayed-release coating) and methods of modifying the coating are also controlled by the factors previously discussed for reservoir system tacrolimus multiparticulates.

The second membrane or coating for dual coated multiparticulates is a delayed-release coating which is applied over the first sustained-release coating, as disclosed above for tablets, and may be formed from the same materials. It should be noted that the use of the so-called "enteric" materials to practice this embodiment differs significantly from their use to produce conventional enteric dosage forms. With conventional enteric forms, the object is to delay release of the drug until the dosage form has passed the stomach and then to deliver the dose in the duodenum. Dosing of tacrolimus directly and completely to the duodenum may be undesirable, however, due to the side effects sought to be minimized or avoided by this invention. Therefore, if conventional enteric polymers are to be used to practice this embodiment, it may be necessary to apply them significantly more thickly than in conventional practice, in order to delay drug release until the dosage form reaches the lower GI tract. However, it is also possible to effect a sustained or controlled delivery of tacrolimus after the delayed-release coating has dissolved or eroded, therefore the benefits of this embodiment may be realized with a proper combination of delayed-release character with sustained-release character, and the delayed-release part alone may or may not necessarily conform to USP enteric criteria. The thickness of the delayed-release coating is adjusted to give the desired delay property. In general, thicker coatings are more resistant to erosion and, consequently, yield a longer delay.

A first delayed release embodiment according to the invention is a "pH-dependent coated dosage form" such as, e.g., a tablet or a capsule. In the case of a tablet it comprises a tablet core comprising tacrolimus e.g. in a solid solution/dispersion as a multiparticulate product, a controlled release matrix of e.g. HPMC, a disintegrant, a lubricant, and one or more pharmaceutical carriers, such core being coated with a material, preferably a polymer, which is substantially insoluble and impermeable at the pH of the stomach, and which is more soluble and permeable at the pH of the small intestine. Preferably, the coating polymer is substantially insoluble and impermeable at pH<5.0, and water-soluble at pH>5.0. The tablet core may be coated with an amount of polymer sufficient to assure that substantially no release of tacrolimus from the dosage form occurs until the dosage form has exited the stomach and has resided in the small intestine for about 15 minutes or greater, preferably about 30 minutes or greater, thus assuring that minimal tacrolimus is released in the duodenum. Mixtures of a pH-sensitive polymer with a water-insoluble polymer may also be employed. Tablets are coated with an amount of polymer comprising from about 10% to about 80% of the weight of the tacrolimus-containing tablet core. Preferred tablets are coated with an amount of polymer comprising about 15% to about 50% of the weight of the tacrolimus tablet core.

pH-sensitive polymers which are very insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Preferred pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

The delay time before release of tacrolimus, after the "pH-dependent coated tablet" dosage form has exited the stomach, may be controlled by choice of the relative amounts of Eudragit-L® and Eudragit-S® in the coating, and by choice of the coating thickness. Eudragit-L® films dissolve above pH 6.0, and Eudragit-S® films dissolve above 7.0, and mixtures dissolve at intermediate pH's. Since the pH of the duodenum is approximately 6.0 and the pH of the colon is approximately 7.0, coatings composed of mixtures of Eudragit-L® and Eudragit-S® provide protection of the duodenum from tacrolimus. If it is desired to delay release of tacrolimus until the tacrolimus-containing "pH-dependent coated tablet" has reached the colon, Eudragit-S® may be used as the coating material, as described by Dew et al. (Br. J. Clin. Pharmac. 14 (1982) 405-408). In order to delay the release of tacrolimus for about 15 minutes or more, preferably 30 minutes or more, after the dosage form has exited the stomach, preferred coatings comprise from about 9:1 to about 1:9 Eudragit-L®/Eudragit-S®, more preferably from about 9:1 to about 1:4 Eudragit-L®/Eudragit-S®. The coating may comprise from about 3% to about 70% of the weight of the uncoated tablet core. Preferably, the coating comprises from about 5% to about 50% of the weight of the tablet core.

Uses

The solid dispersion and/or solution of the invention or the pharmaceutical composition of the invention may be used in the preparation of an solid oral dosage form such as tablets, capsules or sachets; or for the preparation of granules, pellets microspheres or nanoparticles.

Preferably, the solid dispersion or solid solution is used in the preparation of an immediate release solid dosage form or a delayed release solid dosage form.

Other uses of the solid dispersion or solid solution of the invention is for the preparation of a topical dosage form.

A further advantage of a composition of the present invention is the possibility of obtaining an effective therapeutic response with a decreased dosage compared to traditional oral treatment. Thus it is contemplated that the solid dosage form of the invention, when orally administered to a mammal in need thereof in a dose that is at the most about 85% w/w such as, e.g., at the most about 80% w/w, at the most about 75%, at the most about 70% w/w, at the most about 65% w/w, at the most about 60% w/w, at the most about 55% w/w or at the most about 50% w/w of the dose of tacrolimus administered in the form of Prograf® or a similar commercially available tacrolimus-containing product, is essentially bioequivalent with Prograf® or a similar commercially available tacrolimus-containing product.

Any of the tacrolimus-containing dosage forms, compositions, dispersions or solutions of the invention may improved treatment of conditions that respond to tacrolimus treatment.

Tacrolimus is indicated (or has been suggested) for the treatment of diseases such as, e.g., rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.; graft-versus-host reactions following bone marrow transplantation; autoimmune diseases such as rheumatoid arthritis, systemic lupus erythematosus, Hashimoto's thyroiditis, multiple sclerosis, myasthenia gravis, type I diabetes, etc.; infections caused by pathogenic microorganisms (e.g. *Aspergillus fumigatus, Fusarium oxysporum, Trichophyton asteroides*, etc.); inflammatory or hyperproliferative skin diseases or cutaneous manifestations of immunologically mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata); autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.); reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.; mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases); intestinal inflammations/allergies (e.g. coeliac diseases, proctitis, eosinophilic gastroenteritis, mastocytosis, Crohn's disease and ulcerative colitis); food-related allergic diseases with symptomatic manifestation remote from the gastrointestinal tract (e.g. migraine, rhinitis and eczema); renal diseases (e.g. intestitial nephritis, Goodpasture's syndrome, hemolytic uremic syndrome, and diabetic nephropathy); nervous diseases (e.g. multiple myositis, Guillain-Barre syndrome, Meniere's disease, multiple neuritis, solitary neuritis, cerebral infarction, Alzheimer's diseases Parkinson's diseases, amyotrophic lateral sclerosis (ALS) and radiculopathy); cerebral ischemic disease (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), hypertensive encephalopathy, cerebral infarction); endocrine diseases (e.g. hyperthyroidism, and Basedow's disease); hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia); bone diseases (e.g. osteoporosis); respiratory diseases (e.g. sarcoidosis, pulmonary fibrosis, and idiopathic interstitial pneumonia); skin diseases (e.g. dermatomyositis, leukoderma vulgaris, ichthyosis vulgaris, photosensitivity, and cutaneous T-cell lymphoma); circulatory diseases (e.g. arteriosclerosis, atherosclerosis, aortitis syndrome, polyarteritis nodosa, and myocardosis); collagen diseases (e.g. scleroderma, Wegener's granuloma, and Sjogren's syndrome); adiposis; eosinophilic fasciitis; periodontal diseases (e.g. damage to gingiva, periodontium, alveolar bone or substantia ossea dentis); nephrotic syndrome (e.g. glomerulonephritis); male pattern alopecia, alopecia senile; muscular dystrophy; pyoderma and Sezary syndrome; chromosome abnormality-associated diseases (e.g. Down's syndrome); Addison's disease; active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.)); intestinal diseases (e.g. endotoxin shock, pseudomembranous colitis, and drug- or radiation-induced colitis); renal diseases (e.g. ischemic acute renal insufficiency, chronic renal failure); pulmonary diseases (e.g. toxicosis caused by pulmonary oxygen or drugs (e.g. paracort, bleomycin, etc.), lung cancer, and pulmonary emphysema); ocular diseases (e.g. cataracta, iron-storage disease (siderosis bulbi), retinitis, pigmentosa, senile plaques, vitreous scarring, corneal alkali burn); dermatitis (e.g. erythema multiforme, linear immunoglobulin A bullous dermatitis, cement dermatitis); and other diseases (e.g. gingivitis, periodontitis, sepsis, pancreatitis, and diseases caused by environmental pollution (e.g. air pollution), aging, carcinogen, metastasis of carcinoma, and hypobaropathy)]; diseases caused by histamine release or leukotriene C4 release; restenosis of coronary artery following angioplasty and prevention of postsurgical adhesions; autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis); Human Immunodeficiency Virus (HIV) infection, AIDS; allergic conjunctivitis; hypertrophic cicatrix and keloid due to trauma, burn, or surgery.

In addition, tricyclic macrolides like e.g. tacrolimus have liver regenerating activity and/or activities of stimulating hypertrophy and hyperplasia of hepatocytes. Therefore, the pharmaceutical composition of the present invention is useful for increasing the effect of the therapy and/or prophylaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

Furthermore, a composition of the present invention is useful for increasing the effect of the prevention and/or treatment of various diseases because of the useful pharmacological activity of the tricyclic macrolides, such as augmenting activity of chemotherapeutic effect, activity of cytomegalovirus infection, anti-inflammatory activity, inhibiting activity against peptidyl-prolyl isomerase or rotamase, antimalarial activity, antitumor activity and so on.

Materials and Methods

Materials

Tacrolimus (supplied by Eurotrade); batch no RD 03-111
Lactose monohydrate 200 mesh (from DMV)
Granulated silicium oxide, Aeroperl® 300, (Degussa)
Polyethylene glycol 6000, Pluracol® E6000 (from BASF)
Poloxamer 188, Pluronic® F-68 (from BASF)
Glyceryl monostearate, Rylo® MD50, (from Danisco Cultor), Ph.Eur.; batch no. 4010056276
Avicel PH200 (microcrystalline cellulose) (from FMC)
Lactose DCL 11 (from DMV)
Magnesium stearate
Croscarmellose sodium, Ac-Di-Sol® (from FMC)
Eudragit® L30D.55 (from Degussa)
Triethyl citrate (from Merck)
Anti-foam emulsion (from Unikem)
Micro talc
HPMC refers to Metolose 90SH (type 2910, 2208) or Metolose 60SH (type 2910) from ShinEtsu available in various degrees of polymerization (viscosity 3-100,000 cP).

Tablets, capsules or granules might be enteric coated with different types of polymers such as hydroxypropylmethylcellulose acetate succinate (Aqoat), cellulose acetate phtalate CAP, hydroxypropylmethylcellulose phtalate HPMCP or methacrylic acid copolymers such as Eudragit L30D, Eudragit 100/S, Eudragit 100/L.

Comparison Prior Art Tacrolimus Formulation for In Vivo Studies:
Prograf® Hard Gelatin Capsules, manufactured by Fujisawa Ireland Ltd.

| Ingredients | mg |
|---|---|
| Tacrolimus, anhydr. | 1.0 |
| Gelatin | 6.9 |
| Hypromellose | 1.0 |
| Lactose monohydrate | 24.7 |
| Magnesium stearate | 0.3 |
| Shellac | q.s. |
| Soybean lecitine | q.s. |
| Iron oxide red (E172) | q.s. |
| Titanium dioxide (E171) | q.s. |
| Dimeticone (E900) | q.s. |

Methods

Determination of Weight Variation

The tablets prepared in the Examples herein were subjected to a test for weight variation performed in accordance with Ph. Eur.

Determination of Average Tablet Hardness

The tablets prepared in the Examples herein were subjected to at test for tablet hardness employing Schleuniger Model 6D apparatus and performed in accordance with the general instructions for the apparatus.

Determination of Disintegration Time

The time for a tablet to disintegrate, i.e. to decompose into particles or agglomerates, was determined in accordance with Ph. Eur.

Determination of Geometric Weight Mean Diameter $d_{gw}$

The geometric weight mean diameter was determined by employment of a method of laser diffraction dispersing the particulate material obtained (or the starting material) in air. The measurements were performed at 1 bar dispersive pressure in Sympatec Helos equipment, which records the distribution of the equivalent spherical diameter. This distribution is fitted to a log normal volume-size distribution.

When used herein, "geometric weight mean diameter" means the mean diameter of the log normal volume-size distribution.

In Vitro Dissolution Tests

The following test methods were applies to the compositions and dosage forms of the present invention.

Test 1:

In vitro dissolution test according to USP Method A, delayed release articles (USP paddle method; rotation speed: 50 rpm; 37° C.; after 2 hours in acidic medium, the medium is changed to phosphate buffer pH 6.8.).

Test 2:

In vitro dissolution test in aqueous dissolution medium adjusted to pH 4.5 (900 ml water with 0.005% HPC (hydroxypropylcellulose) adjusted to pH4.5; 37° C.; USP Paddle method; rotation speed: 50 rpm).

In Vivo Studies in Beagle Dogs

In vivo studies with the purpose of determining the bioavailability of the compositions of the present invention relative to the bioavailability of the commercially available tacrolimus product, i.e. Prograf®, was performed using Beagle dogs.

The experimental work was performed in Denmark using male Beagle dogs each having a body weight of 12-18 kg (starting weight). The studies were conducted as open, non-randomised, cross-over studies. Each animal was its own control. The dogs were premedicated with Primperan inj. 5 mg/ml (anti-emetica) and an oral dose of 0.5 to 4 mg of tacrolimus was administered.

The dogs were fasted for 10 hours prior to dosing (water ad libitum) and were fed 5 hours after dosing (water ad libitum). Each dog was dosed with the specified dose of tacrolimus without taking the weight of the dog into consideration.

Blood samples were collected at vena jugularis externa at the following points of time:

Pre-dose, 1, 1.5, 2, 3, 4, 6, 8, 12 and 24 hours after dosing. 4 ml of blood were collected, mixed with EDTA, and the samples were frozen (−80° C.). The blood samples were analyzed using on-line extraction LC/MS and results were given in ng/mL.

The determined full blood concentration profiles of tacrolimus were treated using the Pharmacokinetic softwear WinNonlin®, (Pharsight, California; USA) to calculate the pharmacokinetic parameters. All data are dose adjusted.

In Vivo Studies in Göttingen Mini-Pigs

In vivo studies with the purpose of determining the bioavailability of the compositions of the present invention relative to the bioavailability of the commercially available tacrolimus product, i.e. Prograf®, was performed using Göttingen mini-pigs.

The experimental work was performed in Denmark using female mini-pigs having a body weight of 15-18 kg (starting weight). The studies were conducted as open, non-randomised, cross-over studies. Each animal was its own control. An oral dose of 1 mg of tacrolimus was administered. The mini-pigs were fasted for 24 hours prior to dosing (water ad libitum), the mini-pigs were allowed to eat 24 hours after dosing. Each mini-pig was dosed with the specified dose of Tacrolimus without taking the weight of the mini-pig into consideration.

Blood samples were collected at vena jugularis externa at the following points of time:

Pre-dose, 0.5, 1, 1.5, 2, 3, 4, 6, 8, 12 and 24 hours after dosing. 4 ml of blood were collected, mixed with EDTA, and the samples were frozen (−80° C.). The blood samples were analyzed using on-line extraction LC/MS and results were given in ng/mL.

The determined full blood concentration profiles of tacrolimus were treated using the Pharmacokinetic softwear WinNonlin®, (Pharsight, California; USA) to calculate the pharmacokinetic parameters. All data are dose adjusted.

The following examples serve the purpose of illustration of the invention and are not intended to limiting the scope of the present invention.

Pharmaceutical compositions and dosage forms of the invention are exemplified in examples 1-16. Results of in vitro dissolution tests of compositions and dosage forms of the invention are found in example 17. Results of in vivo comparison studies in Beagle dogs (blood plasma concentration) are found in example 18, and results of in vivo comparison studies in Göttingen mini-pigs (blood plasma concentration) are found in example 19.

Example 1

Modified Release Polydepot Capsule Based on Swelling Hydrocolloid Matrix of Hydroxypropylcellulose

| Substance | % | mg |
|---|---|---|
| Tacrolimus | 0.50 | 1.00 |
| HPMC | 20.00 | 40.00 |
| Lactose 200 mesh | 30.00 | 60.00 |
| PEG 6000 | 34.65 | 69.30 |
| Poloxamer 188 | 14.85 | 29.70 |
| Total | 100.00 | 200.00 |

Tacrolimus was dissolved in polyethylene glycol 6000 and poloxamer 188 (70:30 w/w ratio) at 70° C. The solution was sprayed on a mixture of 150 g lactose and 100 g HPMC in a fluid bed Strea-1. The granular product was sieved through sieve 0.7 mm and filled into hard gelatine capsules (200 mg).

Example 2

Modified Release Polydepot Capsule Based on Swelling Hydrocolloid Matrix of Hydroxypropylcellulose

| Substance | % | mg |
|---|---|---|
| Tacrolimus | 0.50 | 1.00 |
| HPMC 2910 3 cp | 20.00 | 40.00 |
| Lactose 200 mesh | 30.00 | 60.00 |
| Glyceryl monostearate | 49.50 | 99.00 |
| Total | 100.00 | 200.00 |

Tacrolimus was dissolved in glyceryl monostearate at 70° C. The solution was sprayed on a mixture of 150 g lactose and 100 g HPMC in a fluid bed Strea-1. The granular product was sieved through sieve 0.7 mm and filled into hard gelatine capsules (200 mg).

Example 3

Modified Release Matrix Tablet Based on Swelling Hydrocolloid Matrix of Hydroxypropylcellulose

| Substance | % | mg |
|---|---|---|
| Tacrolimus | 0.50 | 1.00 |
| HPMC | 19.90 | 40.00 |
| Lactose 200 mesh | 29.85 | 60.00 |
| PEG 6000 | 34.48 | 69.30 |
| Poloxamer 188 | 14.78 | 29.70 |
| Magnesium stearate | 0.50 | 1.01 |
| Total | 100.00 | 201.01 |

Tacrolimus was dissolved in polyethylene glycol 6000 and poloxamer 188 (70:30 w/w ratio) at 70° C. The solution was sprayed onto 250 g lactose in a fluid bed Strea-1. The resulting granular product was sieved through sieve 0.7 mm and blended with HPMC and magnesium stearate for 0.5 min in a Turbula mixer.

The mixture was compressed into 8 mm tablets of 1 mg active ingredient (200 mg tablet) with compound cup shaped.

Mean disintegration time: 20 min. Hardness: 45 N

Example 4

Modified Release Matrix Tablet Based on Lipophilic Matrix of Glyceryl Monostearate

| Substance | % | mg |
|---|---|---|
| Tacrolimus | 0.50 | 1.00 |
| Lactose 200 mesh | 49.75 | 100.00 |
| Glyceryl monostearate | 49.25 | 99.00 |
| Magnesium stearate | 0.50 | 1.01 |
|  | 100.00 | 201.01 |

Tacrolimus was dissolved in glyceryl monostearate at 70° C. The solution was sprayed onto 250 g lactose in a fluid bed Strea-1. The granular product was sieved through sieve 0.7 mm and blended with magnesium stearate for 0.5 minutes in a Turbula mixer.

The resulting mixture was compressed into 8 mm tablets of 1 mg active ingredient (200 mg tablet) with compound cup shape.

Mean disintegration time: 20 min. Hardness: 45 N

Example 5

Modified Release Polydepot Capsule Based on Lipophilic Matrix of Glyceryl Monostearate

| Substance | % | mg |
|---|---|---|
| Tacrolimus | 0.50 | 1.00 |
| Lactose 200 mesh | 49.75 | 100.00 |
| Glyceryl monostearate | 49.25 | 99.00 |
| Magnesium stearate | 0.50 | 1.01 |
|  | 100.00 | 201.01 |

Tacrolimus was dissolved in glyceryl monostearate at 70° C. The solution was sprayed onto 250 g lactose in a fluid bed Strea-1. The granular product was sieved through sieve 0.7 mm and filled into hard gelatine capsules (200 mg).

Example 6

Modified Release Polydepot Tablet Based on Lipophilic Matrix of Gelucire® 44/14

| Substance | % | mg |
|---|---|---|
| Tacrolimus | 0.50 | 1.00 |
| Aeroperl® 300 | 49.75 | 100.00 |
| Gelucire® 44/14 | 49.25 | 99.00 |
| Magnesium stearate | 0.50 | 1.01 |
|  | 100.00 | 201.01 |

Tacrolimus was dissolved in Gelucire® at 70° C. The solution was sprayed onto 250 g Aeroperl® in a fluid bed Strea-1. The granular product was sieved through sieve 0.7 mm and filled into hard gelatine capsules (200 mg).

The resulting granulate was compressed into 8 mm tablets of 1 mg active ingredient (tablet weight 200 mg). Tablets were cup shaped.

Mean disintegration time: 25 minutes. Hardness: 43 N.

Example 7

Enteric Coating

Capsules and tablets of examples 1, 2, 3, 5 and 6 were subsequently coated with the following enteric coating in order to obtain a delayed release of active ingredient after administration.

| Ingredients | % |
|---|---|
| Eudragit® L30D | 40 |
| Purified water | 52 |
| Triethyl acetylcitrate | 1.8 |
| Anti-foam emulsion | 0.2 |
| Talc | 6 |
| Total | 100 |

The coating suspension was prepared by mixing triethyl acetylcitrate, antifoam emulsion and purified water in Ultra Turrax apparatus at 9500 rpm for 30 min. After 1 minute talc was added. The mixture was passed through sieve no. 300 and stirred by a magnet stirrer. Eudragit was passed through sieve no. 300 and added the mixture, which was stirred for 5 minutes.

The process conditions of the coating process were the following an inlet temperature of 40° C., an outlet temperature of 31° C., air inlet of 140 cbm per hour and a coating time of approx. 50 minutes (300 g of coating material). Approx. 400 g of tablets, or 200 g of capsules were coated.

The film coated tablets and capsules were cured for 48 hours at 30° C. before dissolution testing.

Example 8

Modified Release Matrix Tablet Based on Lipohilic Matrix of Glycerol Monostearate

| Substance | % | mg |
|---|---|---|
| Tacrolimus | 0.95 | 2.00 |
| HPMC, Pharmacoat 606 | 6.75 | 14.29 |
| Lactose monohydrate, lactose 125 mesh | 6.75 | 14.29 |
| Glycerol monostearate, Rylo® MD50 | 30.56 | 64.67 |

-continued

| Substance | % | mg |
|---|---|---|
| Magnesium Stearate | 0.5 | 1.06 |
| Talc | 4.5 | 9.52 |
| Lactose monohydrate, Pharmatose DCL 14 | 50.00 | 105.8 |
| | 100.00 | 211.64 |

Tacrolimus was dissolved in glycerol monostearate at a temperature above 80° C. The solution was sprayed by feed unit Phast FS1.7 onto 60 g lactose and 60 g HPMC in a fluid bed Phast FB100. The granular product was hardened in a heating oven for 4 hours at 50° C. The resulting granular product was sifted through sieve 0.71 mm and blended with lactose for 3 minutes in a Turbula mixer.

Magnesium stearate and talc was sifted through sieve no. 300 and mixed in a Turbula mixer for 3 minutes. The granulate was mixed with the mixture of magnesium stearate and talc (1:9) for 0.5 minutes in a Turbula mixer.

The final mixture was compressed into 8 mm tablets of 2 mg active ingredient (210 mg tablet) with compound cup shape.

Mean disintegration time: 2 hours. Hardness: 50 N

Example 9

Enteric Coated Tablet with Core Based on PEG 6000/Poloxamer 188 and Enteric Coating Based on Eudragit L30D 55

Tablet Core Composition:

| Substance | % | mg |
|---|---|---|
| Tacrolimus | 1.98 | 2.00 |
| Lactose monohydrate, Lactose 200 mesh | 40.50 | 40.91 |
| PEG 6000 | 33.26 | 33.60 |
| Poloxamer 188, Lutrol 68 | 14.40 | 14.40 |
| Magnesium Stearate | 0.50 | 0.51 |
| Talc | 4.50 | 4.55 |
| Croscarmellose sodium, Ac-di-sol | 5.00 | 5.05 |
| | 100.00 | 101.01 |

The tacrolimus tablet core was produced by dissolving in PEG 6000 at a temperature above 80° C. Poloxamer 188 was added, and the solution was heated to a temperature above 80° C. The solution was sprayed by feed unit Phast FS1.7 on 200 g lactose monohydrate in a fluid bed Phast FB100. The resulting granulate was sifted through a Comill sieve 1397, 4500 rpm, and blended with croscarmellose sodium for 3 minutes in a Turbula mixer.

Magnesium stearate and talc was sifted through sieve no. 300 and mixed in a Turbula mixer for 3 minutes. The granulate was mixed with magnesium stearate and talc (1:9) for 0.5 minutes in a Turbula mixer.

The resulting mixture was compressed into 6 mm tablets of 2 mg active ingredient (100 mg tablet) with compound cup shape.

Mean disintegration time: 7 minutes. Hardness: 65 N

Enteric Coating:

The enteric coating is based on an acrylic polymer Eudragit L30D-55. Eudragit L30D is supplied as an aqueous latex suspension creating a water insoluble film when the water is evaporated during coating. The polymer is insoluble at pH-values below 5.0 and readily soluble at pH-values over 6.0. The film coating composition is:

| Substance | w/w % |
|---|---|
| Eudragit L30D-55 | 40 |
| Water | 52 |
| Triethyl citrate | 1.8 |
| Anti-foam emulsion | 0.2 |
| Talc (micro) | 6 |
| Total | 100 |

The amount of applied film polymer (Eudragit) was based on a calculation of mg film polymer per cm$^2$ tablet surface. The thickness of the enteric coating was 80 µm. A verification of the film thickness applied was based on measuring the increase in tablet height with a digital micrometer. The film coating process was performed in a Phast FB100 fluid bed equipped with a Wurster like insert. The process conditions were: Inlet air temperature 50° C.; Inlet air flow 100 m$^3$ per hour; Product temperature 38° C.; Feed rate 15 g/min.

After coating proper film formation requires curing of the coated tablets ie. 30° C. in 48 hours in an oven. Alternatively the coated tablets more efficiently could be cured at 40° C. in 24 hours.

Example 10

Controlled Release PEG 6000/Poloxamer 188 Tablet Based on a HPMC Matrix.

Tablet Composition:

| Substance | % | mg |
|---|---|---|
| Tacrolimus | 1.21 | 2.00 |
| Lactose monohydrate, Lactose 200 mesh | 24.75 | 40.91 |
| PEG 6000 | 20.33 | 33.60 |
| Poloxamer 188, Lutrol 68 | 8.71 | 14.40 |
| Magnesium Stearate | 0.50 | 0.83 |
| Talc | 4.50 | 7.44 |
| Hydroxypropyl methylcellulose, Metolose 90SH 15000 | 40.00 | 66.12 |
| | 100.00 | 165.29 |

Tacrolimus was dissolved in PEG 6000 at a temperature above 80° C. Poloxamer 188 is added and the solution is heated to a temperature above 80° C. The solution is sprayed by feed unit Phast FS1.7 on 200 g lactose monohydrate in a fluid bed Phast FB100. The granular product is sieved through a Comill, sieve 1397, 4500 rpm, and blended with Hydroxypropyl methylcellulose for 3 min in a Turbula mixer.

Magnesium stearate and talc is sifted through sieve 300 and mixed in a Turbola mixer for 3 min. The granulate is mixed with Magnesium Stearate:Talc (1:9) for 0.5 min in a Turbula mixer.

The mixture is compressed into 8 mm tablets with strength of 2 mg (165 mg tablet with compound cup shape).

Mean disintegration time: 2 hours 34 minutes, Hardness: 50 N

Example 11

Enteric Coated Tablet Formulation. Wet Granulation and Enteric-Coated Tablets
Tablet Composition:

| Ingredient | mg |
| --- | --- |
| Tacrolimus | 2 |
| Lactose | 80 |
| Sodium lauryl sulfate | 10 |
| Kollidon VA64 | 3 |
| Avicel PH200 | 30 |
| Magnesium stearate | 0.5 |
| Total | 125.5 |

The tablet formulation was based on wet granulation in a high shear mixer Pellmix 1/8. 16 g Micronized tacrolimus was mixed with 640 g lactose 125 mesh and 80 g natrium lauryl sulfate in the high shear mixer. A 15% aqueous solution of binder Koillidon VA64 was pumped to the mixture at an impeller speed of 500 rpm at a feed rate of 20 g/min. and subsequently kneaded for 3 minutes at the equal speed. The granulate was dried in a tray dryer and sieved through sieve size 0.7 mm.

The granulate was mixed with 240 g Avicel PH200 for 3 minutes and for and after addition of 4 g magnesium stearate for further 0.5 minute. The mixture was compressed into tablets on a single punch tabletting machine Diaf TM20.

Tablet diameter: 6 mm. Tablet shape: round, compound cup.
The tablets were subsequently coated with an enteric coating of acrylic type as described in example 9.
The amount of applied film polymer (Eudragit) should be based on a calculation of mg film polymer per cm² tablet surface. The thickness of the enteric coating should be 50-80 µm. A verification of the film thickness applied is based on measuring the increase in tablet height with a digital micrometer. The film coating process is performed in a Stre-1 fluid bed equipped with a Wurster insert at the following process conditions:

| Process parameter | Process value |
| --- | --- |
| Product load, g | 400 |
| Inlet air temperature, ° C. | 40 |
| Inlet air flow, m³ per hour | 140 |
| Outlet air temperature, ° C. | 31 |
| Feed rate g/min | 5 |

After coating, proper film formation requires curing of the coated tablets, i.e. 30° C. in 48 hours in an oven. Alternatively the coated tablets more efficiently could be cured at 40° C. for 24 hours.

Example 12

Controlled Release Tablet Formulation Based on Eroding HPMC Matrix
HPMC Added as Part of the Extragranular Phase. Wet Granulation.
Tablet Composition:

| Ingredients | mg |
| --- | --- |
| Tacrolimus | 2 |
| Lactose | 80 |
| Sodium lauryl sulfate | 10 |
| Kollidon VA64 | 3 |
| Avicel PH200 | 30 |
| Metolose SH 90 | 60 |
| Magnesium stearate | 1 |
| Total | 186 |

The tablet formulation was based on wet granulation in a high shear mixer Pellmix 1/8. 16 g Micronized tacrolimus was mixed with 640 g lactose 125 mesh and 80 g natrium lauryl sulfate in the high shear mixer. A 15% aqueous solution of binder Kollidon VA64 was pumped to the mixture at an impeller speed of 500 rpm at a feed rate of 20 g/min and subsequently kneaded for 3 minutes at equal impeller speed. The granulate was dried in a tray dryer and sieved through sieve size 0.7 mm.

The granulate was mixed with 240 g Avicel PH200 and 480 g hydroxypropylmethylcellulose Metolose SH 90 100 cP for 3 minutes and for and after addition of 8 g magnesium stearate for further 0.5 minute. The mixture was compressed into tablets on a single punch tabletting machine Diaf TM20.

Tablet diameter: 7 mm. Tablet shape: round, compound cup.

Example 13

Controlled Release Tablet Formulation Based on Eroding HPMC Matrix
HPMC Added as Part of the Intragranular Phase. Wet Granulation.
Tablet Composition:

| Ingredient | mg |
| --- | --- |
| Tacrolimus | 2 |
| Lactose | 80 |
| Sodium lauryl sulfate | 10 |
| Metolose SH 90 | 80 |
| Avicel PH200 | 60 |
| Magnesium stearate | 2 |
| Total | 234 |

The tablet formulation was based on wet granulation in a high shear mixer Pellmix 1/8. 16 g Micronized tacrolimus was mixed with 640 g lactose 125 mesh and 80 g natrium lauryl sulfate and 640 g hydroxypropylmethylcellulose Metolose SH 90 15.000 cP?in the high shear mixer. Purified water was pumped to the mixture at an impeller speed of 500 rpm at a feed rate of 20 g/min. and subsequently kneaded for 3 minutes. The granulate was dried in a tray dryer and sieved through sieve size 0.7 mm.

The granulate was mixed with 480 g Avicel PH200 for 3 minutes and for and after addition of 16 g magnesium stearate for further 0.5 minute. The mixture was compressed into tablets on a single punch tabletting machine Diaf TM20.

Tablet diameter: 8 mm. Tablet shape: round, compound cup.

Example 14

Controlled Release Tablet Formulation Based on Eroding HPMC Matrix
HPMC Added as Part of the Intragranular Phase. Melt Granulation
Tablet Composition:

| Ingredient | mg |
|---|---|
| Tacrolimus | 2 |
| Lactose | 80 |
| PEG 6000 | 15 |
| Poloxamer 188 | 6 |
| Metolose SH 90 | 80 |
| Avicel PH200 | 60 |
| Magnesium stearate | 2 |
| Total | 245 |

The tablet formulation was based on melt granulation in a high shear mixer Pellmix 1/8. 16 g Micronized tacrolimus was mixed with 640 g lactose 125 mesh and 120 g Polyethylene glycol 6000, 48 g Poloxamer 188 and 640 g hydroxypropylmethylcellulose Metolose SH 90 15.000 cP in the high shear mixer. The jacket of the mixer bowl was heated to 80° C. and the blend was heated at an impeller rotation speed of 1000 rpm until melting point of PEG and Poloxamer. After melting the kneading was continued for 4 minutes at 800 rpm. The granulated was sieved through sieve size of 0.7 mm and cooled on a tray. The granulate was mixed with 480 g Avicel PH200 for 3 minutes and for and after addition of 16 g magnesium stearate for further 0.5 minute. The mixture was compressed into tablets on a single punch tabletting machine Diaf TM20. Tablet diameter: 8 mm. Tablet shape: round, compound cup.

Example 15

Controlled Release Tablet Formulation Based on Eroding Kollidon SR Matrix Added as Part of the Extragranular Phase.
Tablet Composition:

| Ingredient | mg |
|---|---|
| Tacrolimus | 2 |
| Lactose | 80 |
| Sodium lauryl sulfate | 10 |
| Kollidon VA64 | 3 |
| Lactose DC lac14 | 50 |
| Kollidon SR | 60 |
| Magnesium stearate | 1 |
| Total | 206 |

The tablet formulation was based on wet granulation in a high shear mixer Pellmix 1/8. 16 g Micronized tacrolimus was mixed with 640 g lactose 125 mesh and 80 g natrium lauryl sulfate in the high shear mixer. A 15% aqueous solution of binder Kollidon VA64 (Kollidon SR is a mixture of polyvinyl acetate and polyvinylpyrrolidone 80:20) was pumped to the mixture at an impeller speed of 500 rpm at a feed rate of 20 g/min and subsequently kneaded for 3 minutes. The granulate was dried in a tray dryer and sieved through sieve size 0.7 mm.

The granulate was mixed with 400 g lactose DC Lac 14 and 480 g Kollidon SR for 3 minutes and for and after addition of 8 g magnesium stearate for further 0.5 minute. The mixture was compressed into tablets on a single punch tabletting machine Diaf TM20. Tablet diameter: 8 mm. Tablet shape: round, compound cup.

Example 16

Enteric Coated Tablet Formulation (Melt Granulation and Enteric-Coated Tablets)
Tablet Composition:

| Ingredient | mg |
|---|---|
| Tacrolimus | 2 |
| Lactose | 80 |
| PEG 6000 | 15 |
| Poloxamer 188 | 6 |
| Avicel PH200 | 60 |
| Magnesium stearate | 2 |
| Total | 165 |

The tablet formulation was based on melt granulation in a high shear mixer Pellmix 1/8. 16 g Micronized tacrolimus was mixed with 640 g lactose 125 mesh and 120 g Polyethylene glycol 6000, 48 g Poloxamer 188 in the high shear mixer. The jacket of the mixer bowl was heated to 80° C. and the blend was heated at a impeller rotation speed of 1000 rpm until melting point of PEG and Poloxamer. After melting the kneading was continued for 4 minutes at 800 rpm. The granulated was sieved through sieve size of 0.7 mm and cooled on a tray. The granulate was mixed with 480 g Avicel PH200 for 3 minutes and for and after addition of 16 g magnesium stearate for further 0.5 minute. The mixture was compressed into tablets on a single punch tabletting machine Diaf TM20. Tablet diameter: 7 mm. Tablet shape: round, compound cup.

Enteric coating of the tablets is performed in accordance with the procedure described in Example 11.

Example 17

In Vitro Dissolution Data

Compositions and dosage forms according to the previous examples were subjected to in vitro dissolution tests using two different dissolution media/tests.

A. Using the dissolution medium/test: 900 ml aqueous medium with 0.005% HPC (hydroxypropylcellulose) adjusted to pH=4.5 (USP paddle method; rotation speed: 50 rpm), the following dissolution profiles were found:

| | | | % Release | | | |
|---|---|---|---|---|---|---|
| Time (hours) | Ex. 1 | Ex. 3 | Ex. 4 | Ex. 8 (Rsd %) | Ex. 9 - EC (Rsd %) | Ex. 10 (Rsd %) |
| 0 | 0 | 0 | 0 | 0 (0) | 0 (0) | 0 (0) |
| 0.5 | | | 2 | | | |
| 1 | | | 4 | | | |

-continued

| Time (hours) | Ex. 1 | Ex. 3 | Ex. 4 | Ex. 8 (Rsd %) | Ex. 9 - EC (Rsd %) | Ex. 10 (Rsd %) |
|---|---|---|---|---|---|---|
| | | | | % Release | | |
| 1.5 | 0 | 0 | | | | |
| 2 | 0 | 0 | | | | |
| 3 | | | 6 | | | |
| 4 | 1 | 3 | | 7.8 (11.1) | 0.8 (32.3) | 7.4 (9.8) |
| 5 | | | | | | |
| 6 | 3 | 4 | | | | |
| 8 | 5 | 7 | 17 | 17.0 (8.3) | 0.4 (61.1) | 13.3 (16.5) |
| 10 | 20 | 14 | | | | |
| 15 | 40 | | | 32.2 (4.8) | 11.0 (17.3) | 36.0 (5.8) |
| 16 | | 38 | | | | |
| 17 | | | | 35.1 (9.6) | 13.2 (12.1) | 44.5 (5.4) |
| 20 | | | | | | |
| 24 | | | 37 | | | |

Dissolution profile for tablet cores of Example 9 in dissolution media: 900 ml, aqueous media with 0.005% HPC (hydroxypropylcellulose) adjusted to pH=4.5. USP paddle method. Rotation speed: 50 rpm:

| Time (minutes) | % release | Rsd % |
|---|---|---|
| 0 | 0 | 0 |
| 5 | 27.2 | 15.1 |
| 10 | 49.1 | 10.9 |
| 20 | 80.7 | 8.0 |
| 35 | 98.9 | 5.4 |
| 42 | 102.7 | 3.6 |
| 52 | 104.9 | 2.0 |

Dissolution profile for enteric coated tablets example 9 in dissolution medium accord. to USP Method A, delayed release articles. USP Paddle method. Rotation speed: 50 rpm:

| Time (minutes) | % release | Rsd % |
|---|---|---|
| 0 | 0 | NA |
| 120 | 0 | NA |
| 155 | 84.8 | 12.8 |
| 165 | 102.9 | NA |
| 175 | 101.0 | 3.5 |

Example 18

In Vivo Data (Blood Plasma Concentration; Beagle Dogs)
A. The Following Tacrolimus Formulation was Prepared:

| Substance | % | mg |
|---|---|---|
| Tacrolimus | 0.89 | 1.00 |
| HPMC Pharmacoat 606 | 20.37 | 22.81 |
| Lactose 200 mesh | 20.37 | 22.81 |
| Glyceryl monostearat Rylo MD50 | 58.38 | 65.38 |
| Total | 100.00 | 112.00 |

Tacrolimus was dissolved in glyceryl monostearate at 80° C. The solution was sprayed onto a mixture of 100 g lactose and 100 g hydroxypropylmethylcellulose, Pharmacoat 606, in a fluid bed Strea-1 at a feed rate of 37 g/min. The resulting granular product was sifted through sieve no. 0.7 mm and filled into hard gelatine capsules (112 mg).

In vitro dissolution test (Dissolution media: 900 ml, aqueous media adjusted to pH4.5 with 0.005% HPC; USP paddle method; Rotation speed: 50 rpm) of the formulation gave the following result:

| Time (minutes) | % release | SD |
|---|---|---|
| 0.5 | 83.6 | 21.6 |
| 1 | 93.6 | 7.14 |
| 2 | 97.1 | 8.98 |
| 4 | 97.4 | 7.77 |
| 8 | 98.8 | 7.74 |

An in vivo study of this formulation 0.5 mg in a Beagle dog, performed as described above under Methods, relative to Prograf®, 4×1 mg (Batch no.: 1056050), gave the following results:

Blood concentrations (ng/mL) in dog no. F1183, after administration of formulation:

| Time (hr) | Formulation | |
|---|---|---|
| | Prograf (4 mg) | Invention dose adj. To 4 mg |
| 0 | 0 | 0 |
| 0.5 | 0 | 0.7 |
| 1.0 | 5.8 | 4.2 |
| 1.5 | 16.6 | 10.15 |
| 2.0 | 13.7 | 14.0 |
| 3.0 | 5.1 | 10.85 |
| 4.0 | 3.3 | 9.1 |
| 6.0 | 2.4 | 5.6 |
| 8.0 | 2.3 | 4.2 |
| 12.0 | 2.3 | 3.15 |
| 24.0 | 1.2 | 2.1 |

Relative bioavailability based on AUC (invention/Prograf): 151%.

B. The Following Tacrolimus Formulation was Prepared:

| Substance | % | mg |
|---|---|---|
| Tacrolimus | 0.88 | 1.00 |
| HPMC Pharmacoat 606 | 20.78 | 23.69 |

-continued

| Substance | % | mg |
|---|---|---|
| Aeroperl 300 | 20.78 | 23.69 |
| Glyceryl monostearate Rylo MD50 | 57.56 | 65.62 |
| Total | 100.00 | 114.00 |

Tacrolimus was dissolved in glyceryl monostearate at 80° C. The solution was sprayed on a mixture of 100 g of Aeroperl® 300 (magnesium aluminium metasilicate) and 100 g hydroxypropylmethylcellulose, Pharmacoat 606, in a fluid bed Strea-1 at a feed rate of 38 g/min. The granular product was sifted through sieve 0.7 mm and filled' into hard gelatine capsules (114 mg).

An in vivo study of this formulation 0.5 mg in a Beagle dog, performed as described above under Methods, relative to Prograf®, 4×1 mg (Batch no.: 1056050), gave the following results:

Blood concentrations (ng/mL) in dog no. F1184, after administration of formulation:

| Time (hr) | Formulation | |
|---|---|---|
| | Prograf (4 mg) | Invention dose adj. to 4 mg |
| 0 | 0 | 0 |
| 0.5 | 0.8 | 0.35 |
| 1.0 | 17.2 | 8.75 |
| 1.5 | 29.2 | 23.45 |
| 2.0 | 14.6 | 23.8 |
| 3.0 | 7.8 | 16.45 |
| 4.0 | 5.3 | 11.2 |
| 6.0 | 4.0 | 5.95 |
| 8.0 | 3.3 | 4.55 |
| 12.0 | 3.2 | 3.85 |
| 24.0 | 1.6 | 1.75 |

Relative bioavailability based on AUC (invention/Prograf): 130%.

Example 19

In Vivo Data (Blood Plasma Concentration; Göttingen Mini-Pigs)

The following tacrolimus formulation was prepared:

| Substance | % | mg |
|---|---|---|
| Tacrolimus | 0.52 | 1.00 |
| HPMC Pharmacoat 606 | 12.02 | 22.83 |
| Lactose 200 mesh | 12.02 | 22.83 |
| Glyceryl monostearat Rylo MD50 | 34.44 | 65.44 |
| Magnesium stearate | 1.00 | 1.90 |
| Microcrystalline cellulose Avicel PH200 | 40.00 | 76.00 |
| Total | 100.00 | 190.00 |

Tacrolimus was dissolved in glyceryl monostearate at 80° C. The solution was sprayed on a mixture of 100 g lactose and 100 g hydroxypropylmethylcellulose, Pharmacoat 606, in a fluid bed Strea-1 at a feed rate of 43 g/min. The granular product was sifted through sieve 0.7 mm and mixed with 40% Avicel PH200 for 3 minutes in a Turbula blender and subsequently with 1% magnesium stearate for 0.5 minutes. Tablets of 190 mg were compressed on a single punch machine Diaf TM20. Tablet diameter: 8 mm. Tablet shape: round, compound cup. Tablet hardness: 42 N. Disintegration time: >55 min.

In vitro dissolution test (Dissolution media: 900 ml, aqueous media adjusted to pH4.5 with 0.005% HPC; USP paddle method; Rotation speed: 50 rpm) of the formulation gave the following result:

| Time (hours) | Dissolution (%) | SD |
|---|---|---|
| 0.5 | 1.7 | 0.9 |
| 1 | 3.6 | 3.1 |
| 3 | 6.3 | 0.7 |
| 8 | 16.5 | 3.1 |
| 24 | 36.8 | 2.5 |

An in vivo study of this formulation 1 mg (assay 0.91 mg) in a female Göttingen mini-pig, performed as described above under Methods, relative to Prograf® 1 mg (Batch no.: 105605D), gave the following results:

Blood concentrations (ng/mL) in pig no. 108003, after administration of formulation:

| Time (hr) | Formulation | |
|---|---|---|
| | Prograf (1 mg) | Invention (0.91 mg) |
| 0 | 0.02 | 0 |
| 0.5 | 0.07 | 0.94 |
| 1.0 | 0.20 | 1.12 |
| 1.5 | 0.40 | 1.25 |
| 2.0 | 0.57 | 1.32 |
| 3.0 | 0.74 | 1.19 |
| 4.0 | 0.73 | 1.17 |
| 6.0 | 0.59 | 0.88 |
| 8.0 | 0.40 | 0.81 |
| 12.0 | 0.28 | 0.65 |
| 24.0 | 0.21 | 0.29 |
| 48.0 | 0.10 | 0.10 |

Relative bioavailability based on AUC (invention/Prograf): 177%.

The invention claimed is:

1. A method of preparing an oral extended release pharmaceutical composition of tacrolimus, the method comprising:
   (i) dissolving or dispersing tacrolimus in a vehicle to form a first composition, wherein the vehicle is a hydrophilic or water-miscible vehicle;
   (ii) spraying the first composition onto carrier particles; and
   (iii) blending the product of step (ii) with one or more modifying release agents.

2. The method of claim 1, wherein the hydrophilic or water-miscible vehicle is selected from polyethylene glycols, polyoxyethylene oxides, poloxamers, polyoxyethylene stearates, poly-epsilon caprolactone, and mixtures thereof.

3. The method of claim 1, wherein the hydrophilic or water-miscible vehicle is selected from polyvinylpyrrolidones, polyvinyl-polyvinylacetate copolymers (PVP-PVA), polyvinyl alcohol (PVA), polymethacrylic polymers, cellulose derivatives including hydroxypropyl methylcellulose (HPMC), hydroxypropyl cellulose (HPC), methylcellulose, sodium carboxymethylcellulose, hydroxyethyl cellulose, pectins, cyclodextrins, galactomannans, alginates, carragenates, xanthan gums and mixtures thereof.

4. The method of claim 1, wherein the hydrophilic or water-miscible vehicle comprises polyethylene glycol (PEG).

5. The method of claim 4, wherein the polyethylene glycol has an average molecular weight of at least 1500.

6. The method of claim 4, wherein the polyethylene glycol has an average molecular weight of about 6000.

7. The method of claim 1, wherein the hydrophilic or water-miscible vehicle comprises polyethylene glycol (PEG) and poloxamer.

8. The method of claim 7, wherein poloxamer is poloxamer 188.

9. The method of claim 7, wherein the weight ratio of polyethylene glycol to poloxamer is between 1:3 and 10:1.

10. The method of claim 1, wherein the modifying release agents are selected from hydroxypropyl cellulose (HPC), hydroxypropyl methyl cellulose (HPMC), methyl cellulose, poly (N-vinyl-2-pyrrolidinone) (PVP), poly(ethylene oxide) (PEO), poly(vinyl alcohol) (PVA), xanthan gum, carrageenan, and any combination of any of the foregoing.

11. The method of claim 10, wherein the modifying release agent is hydroxypropyl methyl cellulose (HPMC).

12. The method of claim 1, wherein the carrier particles comprise lactose.

13. An oral extended release pharmaceutical composition prepared by the method of claim 1.

* * * * *